United States Patent
Jezek et al.

(10) Patent No.: US 10,532,098 B2
(45) Date of Patent: Jan. 14, 2020

(54) STABILIZED AQUEOUS ANTIBODY COMPOSITIONS

(71) Applicant: Arecor Limited, Little Chesterford, Saffron Walden (GB)

(72) Inventors: Jan Jezek, Saffron Walden (GB); Guy Casy, Saffron Walden (GB); Barry Kingston Derham, Saffron Walden (GB); Nikki Royle, Saffron Walden (GB)

(73) Assignee: Arecor Limited, Cambridge (GB)

( * ) Notice: Subject to any disclaimer, the term of this patent is extended or adjusted under 35 U.S.C. 154(b) by 510 days.

(21) Appl. No.: 14/375,257

(22) PCT Filed: Jan. 30, 2013

(86) PCT No.: PCT/GB2013/050211
§ 371 (c)(1),
(2) Date: Jul. 29, 2014

(87) PCT Pub. No.: WO2013/114112
PCT Pub. Date: Aug. 8, 2013

(65) Prior Publication Data
US 2015/0010548 A1    Jan. 8, 2015

Related U.S. Application Data

(60) Provisional application No. 61/592,323, filed on Jan. 30, 2012.

(51) Int. Cl.
| *A61K 39/395* | (2006.01) |
| *C07K 16/24* | (2006.01) |
| *C07K 16/28* | (2006.01) |
| *A61K 39/00* | (2006.01) |

(52) U.S. Cl.
CPC ...... *A61K 39/39591* (2013.01); *C07K 16/241* (2013.01); *C07K 16/2887* (2013.01); *A61K 2039/505* (2013.01); *C07K 2317/24* (2013.01)

(58) Field of Classification Search
None
See application file for complete search history.

(56) References Cited

U.S. PATENT DOCUMENTS

| 5,824,784 | A | 10/1998 | Kinstler et al. |
| 5,990,237 | A | 11/1999 | Bentley et al. |
| 2004/0248842 | A1 | 12/2004 | Wagner et al. |
| 2005/0031579 | A1 | 2/2005 | Schluep |
| 2007/0036866 | A1 | 2/2007 | Kissel et al. |
| 2007/0172482 | A1* | 7/2007 | Sagi ............... A61K 39/395 424/146.1 |
| 2010/0172862 | A1* | 7/2010 | Correia ............ A61K 9/0019 424/85.2 |
| 2013/0209465 | A1* | 8/2013 | Jezek ............ A61K 39/39591 424/134.1 |

FOREIGN PATENT DOCUMENTS

| WO | WO02/065963 A1 | 8/2002 |
| WO | WO-2005072121 A2 | 8/2005 |
| WO | WO-2006096461 A2 | 9/2006 |
| WO | WO2007/133812 A2 | 11/2007 |
| WO | WO-2008084237 A2 | 7/2008 |
| WO | WO2008/151150 A2 | 12/2008 |
| WO | WO-2010035001 A1 | 4/2010 |
| WO | WO 2010/062896 A1 | 6/2010 |
| WO | WO-2011141926 A2 | 11/2011 |
| WO | WO 2012/013980 A1 | 2/2012 |
| WO | WO-2013114112 A2 | 8/2013 |

OTHER PUBLICATIONS

Yan, H., et al., "Rapid analysis of charge variants of monoclonal antibodies with capillary zone electrophoresis in dynamically coated fused-silica capillary," *J. Sep. Sci.*; 34: 548-555; Wiley-Vch Verlag GmbH & Co., KGaA, Weinheim (2011).

Communication pursuant to Rule 164(2)(b) and Article 94(3) EPC, dated Jan. 27, 2016, issued in connection with corresponding European Application No. 13 703 468.2.

Torosantucci, R., et al., "Triethlenetetramine prevents insulin aggregation and fragmentation during copper catalyzed oxidation," *European Journal of Pharmaceutics and Biopharmaceutics*; 84: 464-471; Elsevier B.V. (2013).

Akiyama, Y., et al., "Synthesis of Poly(ethylene glycol)-Block-Poly(ethylenimine) Possessing an Acetal Group at the PEG End," Macromolecules 33: 5841-5845, American Chemical Society, United States (2000).

Arnida, et al., "PEGylated Gene Nanocarriers Based on Block Catiomers Bearing Ethylenediamine Repeating Units Directed to Remarkable Enhancement of Photochemical Transfection," Journal of Controlled Release 115(2):208-215, Elsevier Science Publishers, Netherlands (2006).

International Search Report and Written Opinion for International Application Patent No. PCT/GB2013/050211, European Patent Office, Netherlands, dated Sep. 5, 2013.

Knorr, V., et al., "An Acid Sensitive Ketal-Based Polyethylene Glycol-Oligoethylenimine Copolymer Mediates Improved Transfection Efficiency at Reduced Toxicity," Pharmaceutical Research 25(12):2937-2945, Kluwer Academic/Plenum Publishers, New York (2008).

Mazzaferro, L., et al., "Polyethyleneimine-protein interactions and implications on protein stability," International Journal of Biological Macromolecules 47:15-20, Elsevier B.V., Netherlands (2010).

Petersen, H., et al., "Synthesis, Characterization, and Biocompatibility of Polyethylenimine-graft-Poly(ethlene glycol) block copolymers," Macromolecules 35: 6867-6874, American Chemical Society, United States (2002).

(Continued)

*Primary Examiner* — Yunsoo Kim
(74) *Attorney, Agent, or Firm* — Nixon & Vanderhye P.C.

(57) ABSTRACT

The present invention provides an aqueous solution comprising an antibody protein at a concentration of at least about 10 mg/mL and an oligomer of ethyleneimine, wherein the number of repeating units of ethyleneimine (n) in the oligomer is in the range n=2-12.

26 Claims, 6 Drawing Sheets

(56) References Cited

OTHER PUBLICATIONS

Philipp, A., et al., "Functional modification of amide-crosslinked oligoethylenimine for improved siRNA delivery," Reactive and Functional Polymers 71(3):288-293, Elsevier Science Publisher B.V., Netherlands (2010).

Yuan, X., et al., "High PEGylation efficiency of pentaethylenehexamine-end poly(ethylene glycol) (mPEG-N6) for active-ester surface," Colloids and Surfaces. B. Biointerfaces 92:25-29, Elsevier, Netherlands (2012).

Yuan, X., et al., "High-performance Immunolatex Possessing a Mixed-PEG/antibody Coimmobilized Surface: Highly Sensitive Ferritin Immunodiagnostics," Analytical Chemistry 81(4):1549-1556, American Chemical Society, United States (2009).

Andersson, M., et al., "Protein stabilising effect of polyethyleneimine," Journal of Biotechnology 72(1-2):21-31, Elsevier Science, Netherlands (1999).

Bryjak, J., et al., "Storage stabilization and purification of enzyme by water-soluble synthetic polymers," Enzyme and Microbial Technology 16(7):616-621, Butterwork-Heinmann, United Kingdom (1994).

International Search Report for International Application No. PCT/GB2011/051440, dated Feb. 2, 2012.

Scientific Discussion, EMEA, 2005 (29 pages).

Written Opinion for International Application No. PCT/GB2011/051440, dated Jan. 30, 2013.

Merdan et al., Pegylated Polyethylenimine-Fab' Antibody Fragment Conjugates for Targeted Gene Delivery to Human Ovarian Carcinoma Cells, Biocon. Chem., 2003, 14(5), pp. 989-996.

Germershaus et al., Trastuzumab-Polyethylenimine-Polyethylene Glycol Conjugates for Targeting Her2-Expressing Tumors, Biocon. Chem., 2006, 17(5), pp. 1190-1199.

Ahn et al., Biodegradable poly(ethylenimine) for plasmid DNA delivery, J. Cont. Rel., 2002, 80(1-3), pp. 273-282.

Petersen et al., Polyethylenimine-graft-Poly(ethylene glycol) Copolymers: Influence of Copolymer Block Structure on DNA Complexation and Biological Activities as Gene Delivery System, Biocon. Chem., 2002, 13(4), pp. 845-854.

Shuai et al., Novel Biodegradable Ternary Copolymers hy-PEI-g-PCL-b-PEG: Synthesis, Characterization, and Potential as Efficient Nonviral Gene Delivery Vectors, Macromol., 2003, 36(15), pp. 5751-5759.

\* cited by examiner

STABILIZED AQUEOUS ANTIBODY COMPOSITIONS

CROSS-REFERENCE TO RELATED APPLICATIONS

This application is a National Phase of International Application Number PCT/GB2013/050211, filed Jan. 30, 2013, which is incorporated by reference herein.

BACKGROUND OF THE INVENTION

Although a variety of chemical processes, such as oxidation, deamidation and aspartate isomerisation, may affect critical quality attributes of therapeutic proteins, such as antibodies, protein aggregation is arguably the most common process affecting protein stability. Aggregation is typically exacerbated and is the key degradation pathway of proteins formulated in aqueous solution at high concentrations, such as 10 mg/ml or greater. During storage, aggregation can lead to an unacceptably high level of high molecular weight species (HMWS) in the formulation or to formation of larger insoluble aggregates (particulates). Such contaminated formulations may fall outside the specification set by the U.S. Food and Drug Administration and other pharmaceutical regulatory authorities.

To some extent, protein aggregation can be controlled by optimization of various parameters of the protein composition. For example, methods to control the rate of aggregation may involve optimization of pH, addition of a metal ion chelator or addition of a surfactant.

The ionic strength of the composition can also affect the rate of aggregation in aqueous protein compositions. Conventional formulation development for a therapeutic protein therefore typically includes screening of tonicity modifiers, which can be selected from uncharged chemical species, such as sugars, or a charged chemical species, such as an inorganic or an organic salt. An uncharged tonicity modifier is typically preferred if the rate of aggregation is lower in low ionic strength compositions, while a charged tonicity modifier is preferred if the rate of aggregation is lower in higher ionic strength compositions. The charged tonicity modifiers typically used in aqueous protein compositions for therapeutic applications include sodium chloride. Typical uncharged tonicity modifiers include sucrose, trehalose, glycerol and mannitol.

Protein aggregation is a very complex process, involving a number of different mechanisms. However, it is believed that two dominant types of non-covalent interactions drive the protein aggregation: (1) hydrophobic interactions between non-polar parts of the protein molecules, and (2) charge-charge interactions between charged regions of the protein molecules. It is believed that in those cases where the rate of aggregation is lower in compositions of higher ionic strength than in compositions of lower ionic strength the key cause of aggregation is due to charge-charge interactions between the protein molecules.

However, it is also of critical importance that solutions and compositions which are capable of controlling protein aggregation exhibit a favourable toxicity profile, if they are to be of use in therapeutic applications. Thus, any additives which may be used to reduce the rate of protein aggregation must themselves have a favourable toxicity profile.

As such, there is a need for improved methods for preparing stable, highly concentrated protein solutions, particularly highly concentrated antibody solutions that have a favourable toxicity profile and are therefore suitable for use in therapeutic applications.

US 2007/0036866 (Kissel et al.) describes cationic block polymers comprising PEI and PEG residues.

SUMMARY OF THE INVENTION

The present invention addresses the problem of aggregation of antibody proteins, in particular, antibody proteins at elevated concentrations. The present invention also addresses the problem of providing concentrated antibody solutions that exhibit favourable toxicity profiles and are suitable for use in therapeutic applications. Application of the present invention is expected to result in considerable reduction of the rate of aggregation in aqueous antibody protein compositions whilst providing compositions which exhibit favourable toxicity profiles and may therefore be of use in therapeutic applications. The present invention also addresses the problem of self-association of antibody proteins and in aqueous compositions of antibody proteins, particularly at high antibody protein concentrations, whilst providing therapeutically useful compositions of antibody proteins that exhibit favourable toxicity profiles.

In one embodiment, the invention relates to an aqueous solution comprising an antibody protein at a concentration of at least about 10 mg/mL and an oligomer of ethyleneimine, wherein the number of repeating units of ethyleneimine (n) in the oligomer is in the range 2-12.

In one embodiment, the invention provides a method of reducing the rate of aggregation of an antibody protein in aqueous solution at a concentration of at least about 10 mg/mL. The method comprises the step of adding to the solution an oligomer of ethyleneimine, wherein n=2-12.

In one embodiment, the invention may provide a method of reducing the rate of viscosity increase during storage, of an aqueous antibody protein solution at an antibody concentration of at least about 10 mg/mL. The method comprises the step of adding to the solution an oligomer of ethyleneimine, wherein n=2-12.

In one embodiment, the invention may provide a method of reducing the rate of undesired fragmentation of antibody proteins in aqueous solution at a concentration of at least about 10 mg/mL, as detected by the formation of low molecular weight species during storage. In particular, such undesired fragmentation may occur in fusion proteins comprising one or more antibody fragments. The method comprises the step of adding to the solution an oligomer of ethyleneimine; wherein n=2-12.

Certain oligomers of ethyleneimine disclosed herein are novel and are therefore claimed as an aspect of the invention. Thus the invention also provides compounds of Formula (V):

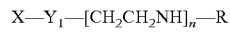

$$X\text{—}Y_1\text{—}[CH_2CH_2NH]_n\text{—}R \qquad \text{Formula V}$$

described in more detail in the following which are useful in the solutions, compositions and methods of the invention.

The solutions and compositions of embodiments described herein are expected to demonstrate favourable toxicity profiles and are therefore suitable for therapeutic applications.

DETAILED DESCRIPTION OF THE INVENTION

Figure 1A:
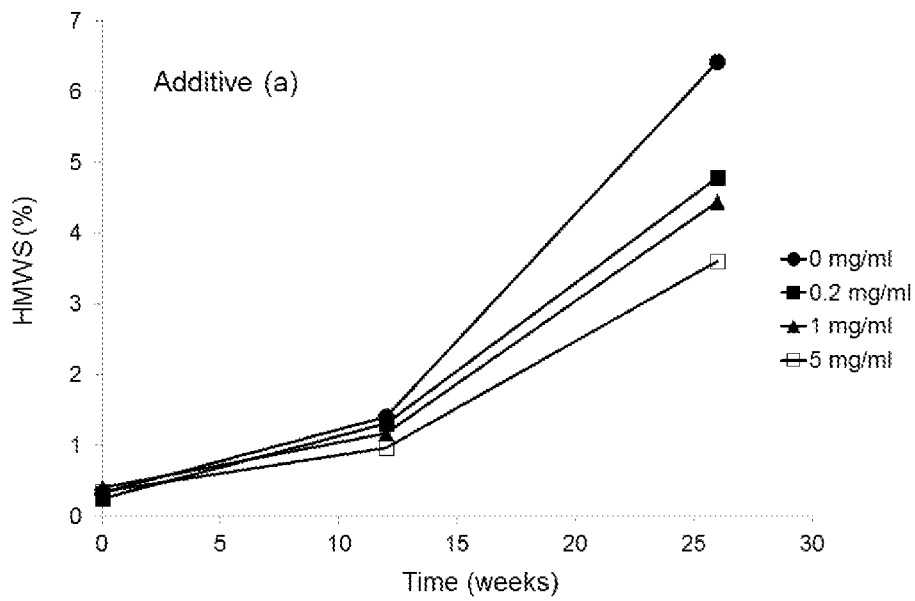
FIGS. 1A-1F show the effect of PEGylated and non-PEGylated oligomers of ethyleneimine and 5k mPEG on the rate of aggregation in formulations of rituximab at 40° C.

The present invention relates to the discovery that oligomers of ethyleneimine wherein n=2-12 stabilize highly concentrated aqueous antibody solutions (i.e. concentrations of at least about 10 mg/mL) whilst being expected to exhibit a favourable toxicity profile. In particular, it is expected that oligomers of ethyleneimine of the present invention exhibit a more favourable toxicity profile than higher homologues (for example, polyethyleneimines with weight greater than 600 Da).

Owing to this expected favourable toxicity profile, the present invention is particularly applicable to aqueous compositions of antibody proteins for therapeutic applications.

Compared with existing methods for stabilizing high concentration aqueous formulations of antibody proteins, particularly with respect to reduced rate of aggregation and reversible self-association, this invention offers several advantages. For example, the present invention should allow a more rational approach to formulation development, requiring less trial and error in designing trial formulations. In turn, this enables an accelerated, lower cost route to an optimized formulation meeting the key performance requirements of storage stability and suitability for low volume subcutaneous injection.

Compared with prior art methods, the stability benefits and expected favourable toxicity profile exhibited by the present invention should enable the use of higher concentration aqueous formulations of therapeutically important antibody proteins.

The term "antibody protein", as used herein, refers to an antibody, an antibody fragment, an antibody conjugated to an active moiety, a fusion protein comprising one or more antibody fragments, such as an immunoglobulin Fc domain, or a derivative of any of the aforementioned. Examples of derivatives include conjugated derivatives e.g. an antibody or antibody fragment conjugated to another moiety. Such moieties include chemically inert polymers such as PEG. Preferred antibodies include monoclonal antibodies and polyclonal antibodies, preferably monoclonal antibodies. The monoclonal antibodies can be, for example, mammalian or avian, chimeric, for example, human/mouse or human/primate chimeras, humanized antibodies or fully human antibodies. Suitable antibodies include an immunoglobulin, such as IgG, including $IgG_1$, $IgG_2$, $IgG_3$ or $IgG_4$, IgM, IgA, such as $IgA_1$ or $IgA_2$, IgD, IgE or IgY. Suitable antibodies also include single chain antibodies. Also included are antibody fragments including Fc, Fab, $Fab_2$, ScFv fragments and the like. Also embraced are single domain antibodies including Nanobodies.

The antibody protein is preferably a therapeutic antibody protein. Such an antibody protein has a desirable therapeutic or prophylactic activity and is indicated for the treatment, inhibition or prevention of a disease or medical disorder.

The term "PEI" refers to a polyethyleneimine, a polymer of ethylenediamine containing multiple repeating groups which may optionally be derivatised.

The term "OEI" refers to an oligomer of ethyleneimine, containing 2-12 repeating units which may optionally be derivatised.

The term "aqueous solution", as used herein, refers to a solution in water, preferably distilled water, deionized water, water for injection, sterile water for injection or bacteriostatic water for injection. The aqueous solutions of the invention include dissolved antibody protein, oligomers of ethyleneimine and, optionally, one or more additives and/or excipients. The aqueous solutions can also include one or more components, such as additives or excipients, which are partially dissolved or undissolved. The presence of such component or components will result in a multi-phase composition, such as a suspension or an emulsion. Preferably, the aqueous solution of the invention is a homogeneous solution, as determined by eye or by light-scattering.

An oligomer of ethyleneimine wherein the number of repeating units of ethyleneimine (n) in the oligomer is in the range 2-12 will typically consist essentially of or comprise a moiety of formula —$(CH_2CH_2NH)_n$— in which n is in the range 2-12, or a branched derivative thereof. A linear ethyleneimine oligomer contains only secondary amino groups (not considering the terminal functionalities of the oligomer), whereas a branched oligomer of polyethylene may contain primary, secondary and tertiary amino groups. In the present invention, aqueous solutions comprising mixtures of linear and branched oligomers of ethyleneimine are also contemplated. Suitably, the ethyleneimine oligomers of the present invention are linear.

For example, n=2, n=3, n=4, n=5, n=6, n=7, n=8, n=9, n=10, n=11, or n=12. In one embodiment, n=3-12, 4-12, 5-12 or 6-12. In a further embodiment, n=2-11, 2-10, 2-9, 2-8, 2-7, 2-6, or 2-5 e.g. 3-5. In a further embodiment, n=3-9, 4-8 or 5-7. In a still further embodiment, n=2-11, 3-11, 4-10, 5-9, or 6-8. In a still further embodiment, n=4-7, 4-6 or 4-5. The oligomer of ethyleneimine wherein n=2-12 may be derivatised or underivatised. In one embodiment, an oligomer of ethyleneimine is underivatised and suitably is selected from the group consisting of diethylenetriamine, triethylenetetramine, tetraethylenepentamine and pentaethylenehexamine. Underivatised oligomers of ethyleneimine are lower in cost and more readily available than the corresponding derivatised oligomers.

The term "oligomer of ethyleneimine" embraces derivatives in which one or more termini of the oligomer are derivatised (e.g. chemically modified) for example by an inert polymer or capping group.

As used herein, '$C_1$-$C_6$alkyl' is defined as a straight or branched aliphatic carbon chain containing 1-6 carbon atoms, for example methyl, ethyl, n-propyl, isopropyl, n-butyl, isobutyl, t-butyl, pentyl, isopentyl, and hexyl, and the corresponding alkylene radicals such as methylene, ethylene, etc.

The oligomer of ethyleneimine can also be derivatised with a chemically inert polymer. As used herein, the term "polymer" includes copolymers unless stated otherwise. The chemically inert polymer can confer a physiochemical benefit to the ethyleneimine oligomer itself, for example by increasing aqueous solubility, increasing stability or reducing toxicity. Alternatively or additionally, the chemically inert polymer may confer a physiochemical benefit to the antibody protein in the aqueous solution, for example by enhancing the effect of the oligomer of ethyleneimine in reducing antibody protein aggregation. In one embodiment, an oligomer of ethyleneimine is derivatised with one or more polymers selected from the group consisting of poly-ethylene glycol (PEG and mPEG (mPEG is a polyethylene glycol polymer that is capped with methoxy)), polypropylene glycol (PPG), and a poly-amino acid. In a further embodiment, an oligomer of ethyleneimine is derivatised with a copolymer, wherein said copolymer consists of polymers (and/or their associated monomers) selected from the group consisting of polyethylene glycol (PEG and mPEG), polypropylene glycol (PPG), and poly-amino acids. Suitable poly-amino acids include those that have uncharged or no side chains and include polyglycine, polyalanine, polyvaline, polyleucine, polyisoleucine and polyphenylalanine. Suitably, an oligomer of ethyleneimine is derivatised with one or more polyethylene glycol (PEG) groups.

When the oligomer of ethyleneimine is derivatised with a chemically inert polymer, typically said polymer has a molecular weight in the range about 500 to about 10000 Da e.g. about 1000 to about 5000 Da.

Polymers polyethylene glycol (e.g. PEG and mPEG), polypropylene glycol (PPG) are defined formulaically as PEG-O—, mPEG-O— and PPG-O— (and likewise copolymers thereof), i.e. a PEG, mPEG, PPG or copolymer molecule terminates with —O— when functioning as a derivative. For example, in the representative formulae PEG -O—$(CH_2CH_2NH)_4$H or PEG-O-OEI, the —O— moiety is associated with the PEG molecule rather than the ethyleneimine oligomer. Against this background, as used herein "PEG" and "PEG-O—" should be taken to be structurally equivalent, only in the latter case, the end group of the PEG has been explicitly defined. In a similar manner, a poly-amino acid is formulaically defined herein to include an amino or carboxy terminus depending on the functionality of the group on the oligomer to which it is bound. For example, in the representative formula [poly-amino acid]-NH—$(CH_2CH_2NH)_4$H, the —NH— moiety is associated with the poly-amino acid. Alternatively, in the representative formula $H_2N$—$(CH_2CH_2NH)_4$—C(O)-[poly-amino acid], the —C(O- moiety is associated with the poly-amino acid.

If present, a chemically inert polymer can be end-capped i.e. the polymer terminates with a functionality that is different to that usually associated with the particular polymer. For example, in one embodiment the chemically inert polymer is polyethylene glycol and is end-capped with a methoxy group i.e. MeOCH$_2$CH$_2$—PEG-O—. As described previously, a polyethylene glycol polymer that is capped with methoxy may be represented as "mPEG". In a preferred embodiment, an oligomer of ethyleneimine is derivatised with one or more PEG or mPEG groups. The PEG or mPEG subunits may be selected for optimum size. In one embodiment, PEG or mPEG is about 500 Da to about 10000 Da, for example about 1000 Da, 2000 Da or 5000 Da. A low polydispersity of PEG and mPEG subunits is desirable. Preferably, the polydispersity is less than 1.2, and more preferably less than 1.1.

An oligomer of ethyleneimine can be derivatised via an optional bridging group i.e. a group that is located between the oligomer of ethyleneimine and the derivatising group (e.g. capping group or carrier group or chemically inert polymer). The optional bridging group preferably has low reactivity and is stable to hydrolysis in aqueous solution in the compositions of the present invention. For example, suitable bridging groups include carbonyl, amide, carbamate, and urea. Optionally an alkylene group (such as $C_2$-$C_{10}$ alkylene or $C_3$-$C_{10}$ alkylene) may intervene between said bridging group and the derivatising group. Preferably, the bridging group is an amide optionally connected to an alkylene group. In an alternative embodiment, the bridging group consists simply of a $C_3$-$C_{10}$ alkylene group, suitably $C_3$-$C_6$ alkylene and more suitably $C_3$ or $C_4$ alkylene, which is connected directly to NH at one terminus of the oligomer of ethyleneimine.

An oligomer of ethyleneimine can be derivatised as described above, wherein one or more termini of the oligomer are derivatised. Alternatively, one or more termini of the oligomer of ethyleneimine can be derivatised and one or more alternative termini of the oligomer can be capped with —H or an inert capping group.

Suitable inert capping groups include —$C_1$-$C_6$alkyl, —($C_2$-$C_6$alkyl)-OH and —($C_2$-$C_6$alkyl)-O—($C_1$-$C_6$alkyl). A preferred capping group is $CH_2CH_2OH$.

Alternatively, an oligomer of ethyleneimine can be underivatised, but can be capped at one or more termini of the oligomer with —H, or an inert capping group as described above.

Any oligomer of ethyleneimine as described above can be linear or branched.

In one embodiment, an oligomer of ethyleneimine of Formula I is provided:

R—K—[CH$_2$CH$_2$NH]$_n$—R            Formula I

wherein K represents O or NH, n=2-12, and each R is independently H or an inert capping group selected from the group consisting of —$C_1$-$C_6$alkyl, —($C_2$-$C_6$alkyl)-OH and —($C_2$-$C_6$alkyl)-O—($C_1$-$C_6$alkyl).

In one embodiment, K represents NH.

In one embodiment, an oligomer of ethyleneimine of formula II is provided:

X—Y$_1$—[CH$_2$CH$_2$NH]$_n$—Y$_2$—X            Formula II

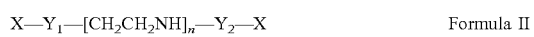

wherein, n=2-12, each X is independently selected from the group consisting of polyethylene glycol (e.g. PEG-O— and mPEG-O—), polypropylene glycol (PPG-O—) and a poly-amino acid; Y$_1$ is optional and is selected from the group consisting of —($C_0$-$C_6$)alkyl-C(O)—NH—, —($C_2$-$C_6$) alkyl-OC(O)—NH—, —($C_2$-$C_6$)alkyl-NHC(O)NH— and —(CH$_2$)$_m$K— wherein m=3-10 and K represents O or NH; Y$_2$ is selected from the group consisting of —C(O)—($C_0$-$C_6$)alkyl-, —C(O)O($C_2$-$C_6$)alkyl-, —C(O)—NH—($C_2$-$C_6$) alkyl- and —(CH$_2$)$_m$— wherein m=2-10.

In one embodiment, optional Y$_1$ is selected from the group consisting of —($C_0$-$C_6$)alkyl-C(O)—NH—, —($C_2$-$C_6$)alkyl-OC(O)—NH—, —($C_2$-$C_6$)alkyl-NHC(O)NH— and —(CH$_2$)$_m$K— wherein m=3-10 and K represents NH.

In one embodiment, optional Y$_1$ is selected from the group consisting of —($C_2$-$C_6$)alkyl-C(O)—NH—, —($C_2$-$C_6$)alkyl-OC(O)—NH—, —($C_2$-$C_6$)alkyl-NHC(O)NH— and (CH$_2$)$_m$K wherein m=3-10 and K represents O or NH.

In one embodiment, optional Y$_1$ is selected from the group consisting of —($C_2$-$C_6$)alkyl-C(O)—NH—, —($C_2$-$C_6$)alkyl-OC(O)—NH—, —($C_2$-$C_6$)alkyl-NHC(O)NH— and (CH$_2$)$_m$K wherein m=3-10 and K represents NH.

In one embodiment, Y$_2$ is selected from the group consisting of —C(O)—($C_2$-$C_6$)alkyl-, —C(O)O($C_2$-$C_6$)alkyl-, —C(O)—NH—($C_2$-$C_6$)alkyl- and —(CH$_2$)$_m$— wherein m=2-10.

In an alternative embodiment, an oligomer of ethyleneimine of formula III is provided:

X—Y$_1$—[CH$_2$CH$_2$NH]$_n$—R            Formula III

wherein, n=2-12; X is selected from the group consisting of polyethylene glycol (e.g. PEG-0- and mPEG-O—), polypropylene glycol (PPG-O—), and a poly-amino acid; $Y_1$ is optional and is selected from the group consisting of —($C_0$-$C_6$)alkyl-C(O)—NH—, —($C_2$-$C_6$)alkyl-OC(O)—NH—, —($C_2$-$C_6$)alkyl-NHC(O)NH— and $(CH_2)_m$K wherein m=3-10 and K represents O or NH; and R is H or an inert capping group selected from the group consisting of —$C_1$-$C_6$alkyl, —($C_2$-$C_6$alkyl)-OH and —($C_2$-$C_6$alkyl)-O—($C_1$-$C_6$alkyl).

In one embodiment, $Y_1$ is optional and is selected from the group consisting of —($C_0$-$C_6$)alkyl-C(O)—NH—, —($C_2$-$C_6$)alkyl-OC(O)—NH—, —($C_2$-$C_6$)alkyl-NHC(O)NH— and $(CH_2)_m$K wherein m=3-10 and K represents NH.

In one embodiment, optional $Y_1$ is selected from the group consisting of —($C_2$-$C_6$)alkyl-C(O)—NH—, —($C_2$-$C_6$)alkyl-OC(O)—NH—, —($C_2$-$C_6$)alkyl-NHC(O)NH and $(CH_2)_m$K wherein m=3-10 and K represents O or NH.

In one embodiment, optional $Y_1$ is selected from the group consisting of —($C_2$-$C_6$)alkyl-C(O)—NH—, —($C_2$-$C_6$)alkyl-OC(O)—NH—, —($C_2$-$C_6$)alkyl-NHC(O)NH and $(CH_2)_m$K wherein m=3-10 and K represents NH.

In one embodiment of Formula (III), n=2-12; X is PEG-O— or mPEG-O—, $Y_1$ is absent and R is —H or —$CH_2CH_2OH$. In a further embodiment, n=2-12; X is mPEG-O—; $Y_1$ is absent and R is —H. In a further embodiment, n=2-12; X is mPEG-O—; $Y_1$ is absent and R is —$CH_2CH_2OH$. In a further embodiment, n=2-8; X is mPEG-O—; $Y_1$ is absent and R is —$CH_2CH_2OH$. In a further embodiment, n=2; X is mPEG-O—; $Y_1$ is absent and R is —$CH_2CH_2OH$. In a further embodiment, n=5; X is mPEG-O—; $Y_1$ is absent and R is —$CH_2CH_2OH$. In a further embodiment, n=8; X is mPEG-O—; $Y_1$ is absent and R is —$CH_2CH_2OH$.

In one embodiment of Formula (III), n=2-12; X is mPEG-O—, $Y_1$ is present and is selected from the group consisting of —($C_0$-$C_6$)alkyl-C(O)—NH—, —($C_2$-$C_6$)alkyl-OC(O)—NH—, —($C_2$-$C_6$)alkyl-NHC(O)NH— and —$(CH_2)_m$K— wherein m=3-10 and K represents O or NH; and R is —H or $CH_2CH_2OH$. In a further embodiment, n=4-8; X is mPEG-O—; Y is —($C_0$-$C_6$)alkyl-C(O)—NH— and R is —H. In a further embodiment, n=5; X is mPEG-O—; Y is —($C_2$)alkyl-C(O)—NH— and R is —H. In a further embodiment, n=5; X is mPEG-O—; Y is —($C_4$)alkyl-C(O)—NH— and R is —H.

In an alternative embodiment, an oligomer of ethyleneimine of formula IV is provided:

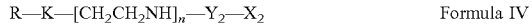

R—K—[$CH_2CH_2NH$]$_n$—$Y_2$—$X_2$     Formula IV wherein, n=2-12, K represents O or NH; $X_2$ is selected from the group consisting of polyethylene glycol (e.g. PEG-O— and mPEG-O—), polypropylene glycol (PPG-O—) and a poly-amino acid; $Y_2$ is selected from the group consisting of —C(O)—($C_0$-$C_6$)alkyl-, —C(O)O($C_2$-$C_6$)alkyl-, —C(O)—NH—($C_2$-$C_6$)alkyl- and —$(CH_2)_m$— wherein m=2-10; and R is —H or an inert capping group selected from the group consisting of —$C_1$-$C_6$alkyl, —($C_2$-$C_6$alkyl)-OH and —($C_2$-$C_6$alkyl)-O—($C_1$-$C_6$alkyl).

In one embodiment of Formula IV, n=2; K represents O, $X_2$ is mPEG-O—; $Y_2$ is —C(O)—($C_2$)alkyl-; and R is —H. Similarly in another embodiment of Formula IV, n=2; K represents O; $X_2$ is mPEG-O—; $Y_2$ is —$(CH_2)_3$—; and R is —H. In one embodiment, $Y_2$ is selected from the group consisting of —C(O)—($C_2$-$C_6$)alkyl-, —C(O)O($C_2$-$C_6$)alkyl-, —C(O)—NH—($C_2$-$C_6$)alkyl- and —$(CH_2)_m$— wherein m=2-10.

Oligomers of ethyleneimine including their derivatives can be prepared by conventional processes for example by steps including:

(i) polymerisation of ethyleneimine or else polymerisation of 2-methyl-2-oxazoline or 2-ethyl-2-oxazoline followed by deacylation by alkaline hydrolysis. For example, this method is applicable for the preparation of oligomers of ethyleneimine derivatised with mPEG, in which an mPEG derivative mPEG-X, wherein X is $NH_2$, OH, O-mesyl or O-tosyl, is employed as an initiating reactant for the polymerisation. Such procedures can be based on those described by Kissel et al. in US20070036866A1 and by Akiyama et al. in Macromolecules, 2000, 33, 5841-5845.

(ii) acylation of a pre-formed oligomer of ethyleneimine by reaction with an activated carboxyl derivative of a carrier polymer. For example, in the case of a carrier polymer based on mPEG, suitable activated carboxyl derivatives are mPEG-succinimidyl propanoate and mPEG-succinimidyl valerate, thereby incorporating an alkyl-amide bridging group. Such procedures can be based on those described by Wagner et al. in US20040248842A1 and Schluep in US20050031579A1.

(iii) reaction of a pre-formed oligomer of ethyleneimine with an isocyanate derivative of a carrier polymer, thereby incorporating an alkyl-urea bridging group. For example, in the case of a carrier polymer based on mPEG, a suitable iscocyanate derivative is prepared from mPEG-alcohol and hexamethylene diisocyanate. Such procedures can be based on those described by Petersen et al. in Macromolecules 2002, 35, 6867-6874.

(iv) reductive amination employing a pre-formed oligomer of ethyleneimine and an aldehyde derivative of a carrier polymer, thereby incorporating a $(CH_2)_m$ bridging group. For example, in the case of a carrier polymer based on mPEG, suitable aldehyde derivatives are mPEG propionaldehyde and mPEG butyraldehyde. The corresponding aldehyde hydrates may also be employed. Such procedures can be based on those utilised in N-terminal PEGylation of proteins, for example as described by Kintsler in U.S. Pat. No. 5,824,784 and by Bentley and Harris in U.S. Pat. No. 5,990,237.

Exemplary conditions are described in the Examples section.

An oligomer of ethyleneimine can be added to the aqueous solution or composition of the invention in the free base form or in the form of a salt. The pH of the aqueous solution or composition is preferably sufficiently low such that at least a portion of the basic groups of the oligomer of ethyleneimine are protonated in solution. Typically the pH of the aqueous solution or composition according to the invention is in the range 4 to 8 e.g. 5.0 to 7.5 or 5.5 to 7.0. Preferably the pH of the aqueous solution or composition according to the invention may be in the ranges 5.5 to 6.0, 6.0 to 6.5 or 6.5 to 7.0.

The oligomer of ethyleneimine can also be added to the aqueous solution or composition as a salt of a suitable acid, such as a pharmaceutically acceptable acid. Suitable acids include hydrochloric acid, hydrobromic acid, citric acid, lactic acid, tartaric acid, phosphoric acid, methanesulfonic acid, acetic acid, formic acid, maleic acid, fumaric acid, malic acid, succinic acid, malonic acid, sulfuric acid, L-glutamic acid, tartaric acid, L-aspartic acid, pyruvic acid, mucic acid, benzoic acid, glucoronic acid, oxalic acid, and ascorbic acid. In one embodiment, the acid is a polyacid comprising two or more acidic groups. It should be noted that although the derivatised oligomers of polyethylene glycol of Formulae I, II, III and IV are depicted with unprotonated nitrogen centres, it is intended that oligomers of these Formulae wherein a portion or indeed all of the basic nitrogen centres are protonated, are also considered to be within the scope of the invention. All embodiments contemplating underivatised oligomers of ethyleneimine wherein a portion or all of the basic nitrogen centres are protonated are also considered to be within the scope of the invention.

In one embodiment, 50-100% of the basic nitrogen centres of an oligomer of ethyleneimine are protonated. In a further embodiment, 80-100% of the basic nitrogen centres of an oligomer of ethyleneimine are protonated. Preferably, at least 95% of the basic nitrogen centres of an oligomer of ethyleneimine are protonated. Without wishing to be bound by theory, it is contemplated that when at least 95% of the basic nitrogen centres of the ethyleneimine oligomer are protonated, the high charge density on the antibody protein surface is masked, thereby inhibiting aggregation of the antibody protein. In particular, without wishing to be bound by theory, it is contemplated that the negatively charged patches at the antibody protein surface are masked by the ethyleneimine oligomer, thereby inhibiting charge-driven aggregation of the antibody protein.

In one embodiment, the pH of the aqueous solution comprising an antibody protein is below the isoelectric point (pI) of the protein. In one embodiment, the pI of the antibody protein is higher than the pH of the solution, suitably at least 0.5 units higher, more suitably at between 0.5 and 5 units higher, even more suitably between 1 and 3 units higher. In one embodiment, the pI of the antibody protein is at least 7, for example in the range 7-10 or 7.5-9.

In one embodiment, the aqueous solution comprising an antibody protein is isotonic. In one embodiment, the aqueous solution comprising an antibody protein is hypertonic. In one embodiment, the aqueous solution comprising an antibody protein is hypotonic.

An oligomer of ethyleneimine is present in the composition at a concentration which is sufficient to provide the desired stability. In one embodiment, the concentration of the oligomer of ethyleneimine is from about 0.01 to about 10 mg/mL, for example from about 0.01 to about 0.1 mg/mL, about 0.1 to about 0.25 mg/mL, about 0.25 to about 1 mg/mL, about 1 to about 2 mg/mL, about 2 to about 5 mg/mL, or about 5 to about 10 mg/mL. In an embodiment, the concentration of the oligomer of ethyleneimine is about 0.2 mg/mL to about 2 mg/mL. As used herein, the mass of oligomer of ethyleneimine in a composition of the invention refers to the free base equivalent, i.e. it does not include any counter anions, if present.

In certain embodiments, the ratio (wt/wt) of antibody protein to oligomer of ethyleneimine is at least 10, for example, at least 20. In certain embodiments the weight ratio of protein to oligomer of ethyleneimine is from about 20 to about 300, preferably from about 50 to about 200. In certain embodiments, the weight ratio of protein to oligomer of ethyleneimine is about 100. In certain embodiments the weight ratio of protein to oligomer of ethyleneimine may be higher than 300, for example up to 500, 800, or 1000. These weight ratios refer to the weight of the ethyleneimine oligomer content per se excluding any derivatising groups (e.g. PEG groups). In one embodiment, the ratio (wt/wt) of antibody protein to oligomer is from about 100 to about 200.

The solutions of the invention preferably comprise a buffer. Typically the buffer is selected to provide a pH that will allow dissolution of the protein to the desired concentration. Preferably, the pH is sufficiently low that at least a portion of the basic groups in the oligomer of ethyleneimine are protonated. The buffer can also be selected to enhance protein stability.

Figure 2:
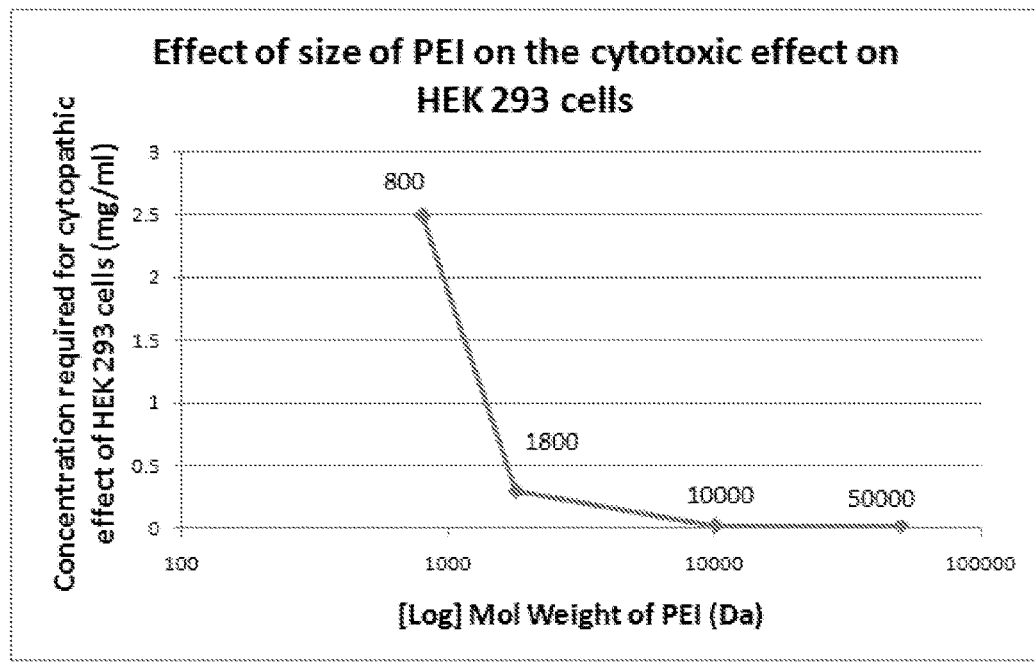
FIG. 2 shows the effect of size of PEI on the cytotoxic effect on HEK 293 and Vero cells.
Figure 2:
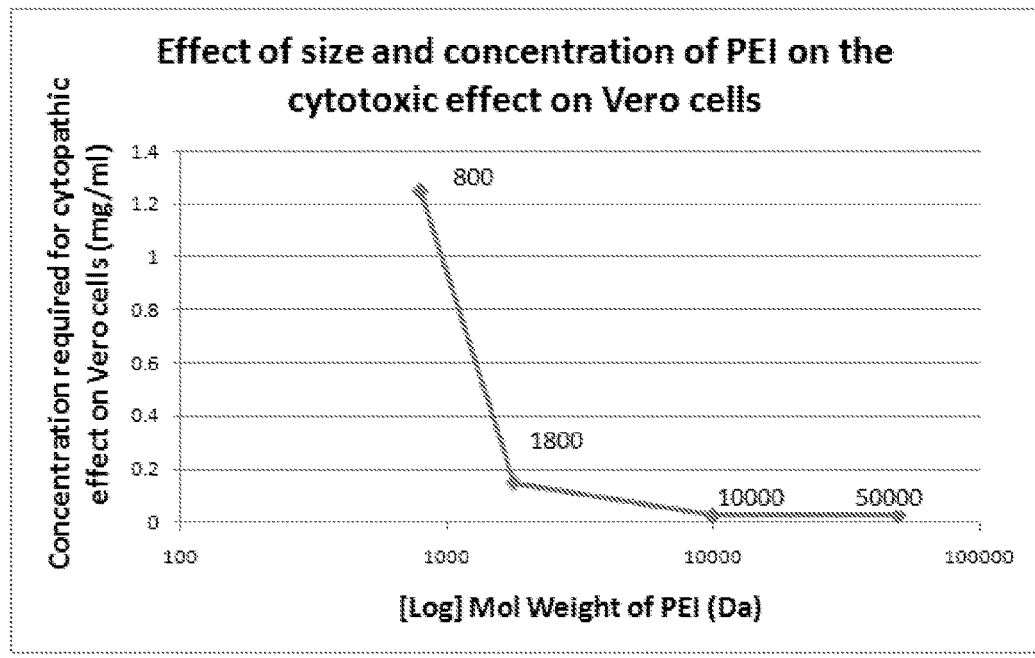
Figure 3:
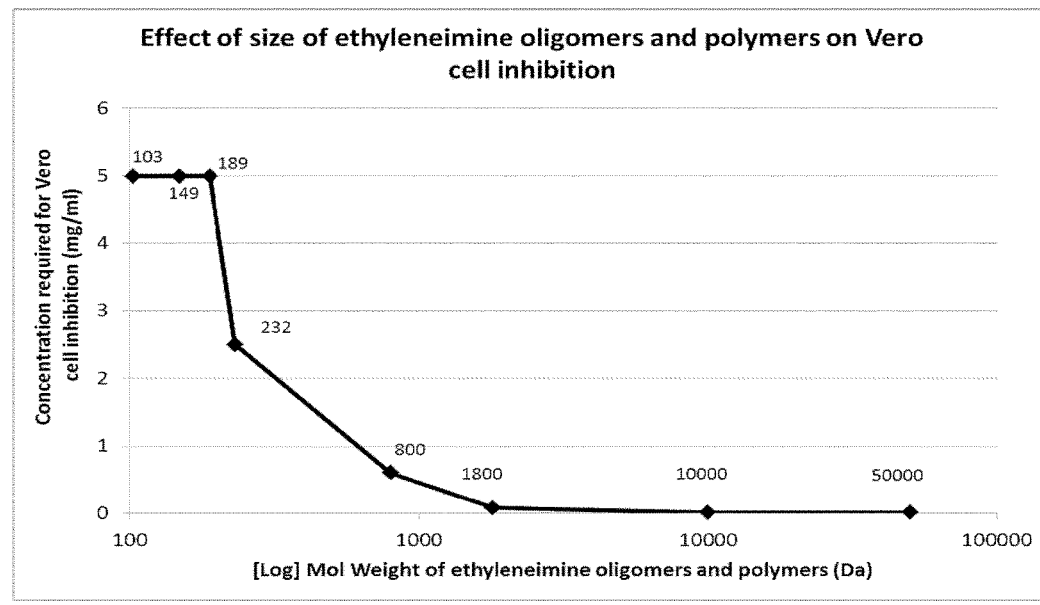
FIG. 3 shows the effect of the size of oligomer of ethyleneimine on Vero cell inhibition. The number beside each point indicates the molecular weight (Da) of the oligomer or polymer tested.
Figure 4:
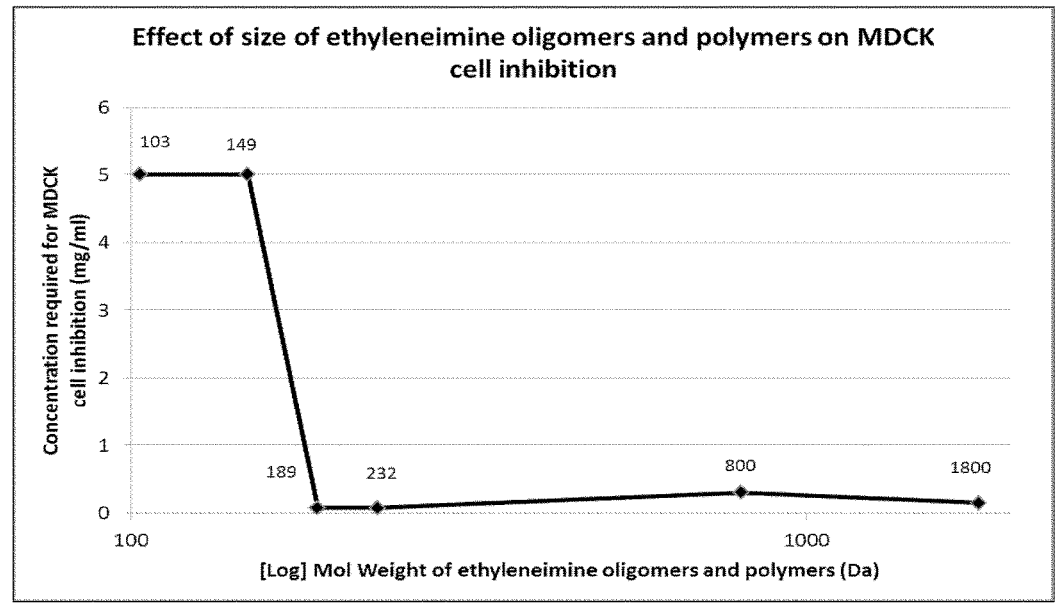
FIG. 4 shows the effect of the size of oligomer of ethyleneimine on MDCK cell inhibition. The number beside each point indicates the molecular weight (Da) of the oligomer tested.

The present inventors have investigated the effect of the size of oligomers and polymers of ethyleneimine on cytotoxicity, as described in Examples 7 and 8. The results are illustrated in FIGS. 2, 3 and 4, and clearly demonstrate that as polyethyleneimine decreases in size, so does its cytotoxic effect. The decreasing cytotoxicity is demonstrated for polyethyleneimine of weight about 50,000 Da decreasing down to about 800 Da (see Example 7). This trend in decreasing cytotoxicity can reasonably be extrapolated to suggest that oligomers of ethyleneimine wherein the number of repeating units of ethyleneimine (n) in the oligomer is in the range 2-12 (i.e. of weight<800 Da) would have even lower cytotoxicity. Indeed, decreasing cytotoxicity is further demonstrated down to about 100 Da (see Example 8). Without wishing to be bound by theory, the present inventors believe that the oligomers of ethyleneimine wherein the number of repeating units of ethyleneimine (n) in the oligomer is in the range 2-12 are of sufficient size to mask regions of the antibody protein surface having a high charge density, thereby solving the problem of antibody protein aggregation in concentrated solutions. In particular, without wishing to be bound by theory, it is contemplated that oligomers of ethyleneimine wherein n=2-12 are of sufficient size to mask patches of the antibody protein having a high negative charge density, thereby solving the problem of charge-driven antibody protein aggregation in concentrated solutions. Moreover, as a result of the inventors' studies (see FIGS. 2, 3 and 4), and again without being bound by any theory, the present inventors believe that oligomers of ethyleneimine wherein the number of repeating units of ethyleneimine (n) in the oligomer is in the range 2-12 are also of a sufficiently small size so as to avoid exerting any toxic effect associated with disruption of cell membranes. Therefore, such oligomers may reduce aggregation in concentrated antibody protein solutions whilst exhibiting a favourable toxicity profile. Accordingly, such oligomers are of particular use in therapeutic applications.

As described in Examples 1-6, it has been found that an oligomer of ethyleneimine defined as herein can significantly reduce the rate of antibody protein aggregation in a composition, such as an aqueous antibody protein solution, compared with a composition lacking said oligomer of ethyleneimine but otherwise similar or identical, following storage under the same conditions and for the same length of time.

In one embodiment, the presence of an oligomer of ethyleneimine wherein the number of repeating units of ethyleneimine (n) in the oligomer is in the range 2-12 in a concentrated aqueous solution of antibody protein limits the increase in high molecular weight protein species to no more than 5% (by weight of total protein) after storage at 40° C. for one month, suitably to no more than 3% and more suitably to no more than 2%. In one embodiment, the presence of an oligomer of ethyleneimine wherein the number of repeating units of ethyleneimine (n) in the oligomer is in the range 2-12 in a concentrated aqueous solution of antibody protein limits the increase in high molecular weight protein species to no more than 5% (by weight of total protein) after storage at 2-8° C. for up to two years, suitably to no more than 3% and more suitably to no more than 2%. Quantitation of high molecular weight species is as percent by weight of the total protein in the composition.

In one embodiment, the presence of an oligomer of ethyleneimine; wherein the number of repeating units of ethyleneimine (n) in the oligomer is in the range 2-12 in a concentrated aqueous solution of antibody protein limits the increase in high molecular weight protein species by at least 10%, preferably by at least 25%, and more preferably by at least 50% compared with a composition lacking the oligomer of ethyleneimine but otherwise identical, following storage under the same conditions and length of time.

In one embodiment, the presence of an oligomer of ethyleneimine wherein the number of repeating units of ethyleneimine (n) in the oligomer is in the range 2-12 in a concentrated aqueous solution of antibody protein maintains an aqueous composition of a protein free of visible aggregates while formation of visible aggregates is observed in a composition lacking the oligomer of ethyleneimine but otherwise identical, following storage under the same conditions and for the same length of time. Quantification of visible aggregates can be performed by turbidity or other types of light scattering measurement.

In certain embodiments, the antibody is fused or conjugated to an active molecule, such as a toxin or a chelating agent capable of binding a radioactive metal ion, such as $^{99}$Tc, $^{111}$Ir, $^{131}$I or $^{90}$Y. In such embodiments, the antibody typically functions as a targeting agent, for example, directing the active molecule to cells which display a certain cell surface protein.

Specific antibodies which can be formulated as described herein include, but are not limited to, infliximab (chimeric antibody, anti-TNFα), adalimumab (human antibody, anti-TNFα), basiliximab (chimeric antibody, anti-IL-2), abciximab (chimeric antibody, anti-GpIIb/IIIa), daclizumab (humanized antibody, anti-IL-2), gemtuzumab (humanized antibody, anti-CD33), alemtuzumab (humanized antibody, anti-CD52), edrecolomab (murine Ig2a, anti-EpCAM), rituximab (chimeric antibody, anti-CD20), palivizumab (humanized antibody, anti-respiratory syncytial virus), trastuzumab (humanized antibody, anti-HER2/neu(erbB2) receptor), bevacizumab (humanized antibody, anti-VEGF), cetuximab (chimeric antibody, anti-EGFR), eculizumab (humanized antibody, anti-complement system protein C5), efalizumab (humanized antibody, anti-CD 11a), ibritumomab (murine antibody, anti-CD20), muromonab-CD3 (murine antibody, anti-T cell CD3 receptor), natalizumab (humanized antibody, anti-α4 integrin), nimotuzumab (humanized IgG1, anti-EGF receptor), omalizumab (humanized antibody, anti-IgE), panitumumab (human antibody, anti-EGFR), ranibizumab (humanized antibody, anti-VEGF), I-131 tositumomab (humanized antibody, anti-CD20), ofatumumab (human antibody, anti-CD-20), certolizumab (humanized antibody, anti-TNF-α), golimumab (human antibody, anti-TNFα) and denosumab (human antibody, anti-RANK ligand). Preferred antibodies include trastuzumab and rituximab. A further antibody of interest is infliximab.

Other chimeric antibodies which can be formulated as described herein include bavituximab (anti-phosphatidylserine), brentuximab (anti-CD30), siltuximab (anti-IL-6), clenoliximab (anti-CD4), galiximab (anti-CD80), gomiliximab (anti-CD23), keliximab (anti-CD4), lumiliximab (anti-CD23), priliximab (anti-CD4), teneliximab (anti-CD40), vapaliximab (anti-VAP1), ecromeximab (anti-GD3), and pagibaximab (anti-staphylococcal lipoteichoic acid).

Other humanized antibodies which can formulated as described herein include epratuzumab (anti-CD22), afutuzumab (anti-CD20), bivatuzumab mertansine (anti-CD44), cantuzumab mertansine (anti-mucin), citatuzumab bogatox (anti-TACSTD1), dacetuzumab (anti-CD40), elotuzumab (anti-CD319), etaracizumab (anti-$\alpha_v\beta_3$-integrin), farletuzumab (anti-FRa), inotuzumab ozogamicin (anti-CD22), labetuzumab (anti-carcinoembryonic antigen), lintuzumab (anti-CD33), milatuzumab (anti-CD74), nimotuzumab (anti-EGFR), oportuzumab monatox (anti-EpCAM), pertuzumab (anti-HER2), sibrotuzumab (anti-FAP), tacatuzumab tetraxetan (anti-alpha-fetoprotein), tigatuzumab (anti-TRAIL-2), tucotuzumab celmoleukin (anti-EpCAM), veltuzumab (anti-CD20), aselizumab (anti-CD62L), apolizumab (anti-HLA-DRB), benralizumab (anti-CD125), cedelizumab (anti-CD4), epratuzumab (anti-CD22), erlizumab (anti-CD18), fontolizumab (anti-interferon-γ), mepolizumab (anti-IL5), ocrelizumab (anti-CD20), pascolizumab (anti-IL4), pexelizumab (anti-complement component 5), PRO-140 (anti-CCR5), reslizumab (anti-IL5), rontalizumab (anti interferon-α), rovelizumab (anti-CD11, CD18), siplizumab (anti-CD2), talizumab (anti-IgE), teplizumab (anti-CD3), tocilizumab (anti-IL6R), vedolizumab (anti-$\alpha_4\beta_7$-integrin), visilizumab (anti-CD3), ibalizumab (anti-CD4), tefibazumab (anti-clumping factor A), tadocizumab (anti-$\alpha_{11b}\beta_3$-integrin), bapineuzumab (anti-amyloid-β), solanezumab (anti-amyloid-β), tanezumab (anti-NGF), urtoxazumab (anti-*E. coli* Shiga-like toxin II B subunit), felvizumab (anti-respiratory syncytial virus), motavizumab (anti-respiratory syncytial virus glycoprotein F) and lebrikizumab (anti-IL13).

Additional human antibodies which can be formulated as described herein include atorolimumab (anti-Rh factor), fresolimumab (anti-TGFβ-1, -2, and -3), lerdelimumab (anti-TGFβ3-2), metelimumab (anti-TGFβ-1), morolimumab (anti-Rh factor), ipilimumab (anti-CTLA-4), tremelimumab (anti-CTLA-4), bertilimumab (anti-CCL11), zanolimumab (anti-CD4), briakinumab (anti-IL12, -23), canakinumab (anti-IL1β), ustekinumab (anti-IL12, -23), adecatumumab (anti-EpCAM), belimumab (anti-B cell activating factor), cixutumumab anti-IGF-1 receptor), conatumumab (anti-TRAIL-R2), figitumumab (anti-IGF-1 receptor), iratumumab (anti-CD30), lexatumumab (anti-TRAIL-R2), lucatumumab (anti-CD40), mapatumumab (anti-TRAIL-R4), necitumumab (anti-EGFR), olaratumab (anti-PDGF-Rα), pritumumab (anti-vimentin), robatumumab (anti-IGF-1 receptor), votumumab (anti-tumor antigen CTAA16.88), zalutumumab (anti-EGFR), stamulumab (anti-myostatin), efungumab (anti-fungal HSP90), exbivirumab (anti-hepatitis B surface antigen), foravirumab (anti-rabies glycoprotein), libivirumab (anti-hepatitis B surface antigen), rafivirumab (anti-rabies glycoprotein), regavirumab (anti-cytomegalovirus glycoprotein B), sevirumab (anti-cytomegalovirus), tuvirumab (anti-hepatitis B virus), panobacumab (anti-*Pseudomonas aeruginosa* serotype IATS 011), raxibacumab (anti-anthrax toxin), ramucirumab (anti-VEGF-R2), and gantenerumab (anti-amyloid-β).

Fusion proteins comprising a fragment of an immunoglobulin molecule can also be formulated according to the invention. Suitable fusion proteins include proteins comprising an active protein domain fused to one or more immunoglobulin fragments, such as Fc domains. Such fusion proteins include dimeric proteins having monomeric units comprising an active protein domain, such as a soluble receptor or a receptor extracellular ligand binding domain, which is fused to an immunoglobulin Fc domain. Two Fc domains can associate via disulfide bonds to form the dimeric protein. Such fusion proteins include etanercept, abatacept and belatacept.

Conjugated derivatives comprising antibodies (or one or more antibody fragments) and a chemically inert polymer such as PEG can also be formulated according to the invention. Such derivatives include certolizumab pegol.

The antibody protein can be isolated from natural sources or be a recombinant protein.

In certain embodiments, the antibody protein is substantially pure, that is, the composition comprises a single protein and no substantial amount of any additional protein.

In preferred embodiments, the protein comprises at least 99%, preferably at least 99.5% and more preferably at least about 99.9% of the total protein content of the composition. In preferred embodiments the protein is sufficiently pure for use as in a pharmaceutical composition.

The concentration of the antibody protein in the aqueous solution is at least about 10 mg/mL, and is preferably in the range of about 25 mg/mL to about 400 mg/mL. In certain embodiments the concentration is at least about 25 mg/mL. In certain embodiments, the protein concentration is at least about 30 mg/mL, 40 mg/mL, 50 mg/mL, 60 mg/mL, 70 mg/mL, 80 mg/mL, 90 mg/mL or 100 mg/mL. More preferably the protein concentration is greater than 50 mg/mL e.g. at least about 80 mg/mL. The concentration can be up to about 400 mg/mL, for example up to about 350 mg/mL, 300 mg/mL, 250 mg/mL, 200 mg/mL or 175 mg/mL. Every concentration range bounded by one of the foregoing lower limits and one of the foregoing upper limits is contemplated herein.

The term "pharmaceutically acceptable", as used herein, refers to components of a pharmaceutical composition which are suitable for the intended use and mode of administration to the body of a human or an animal, such as a mammal, without undue adverse consequences, such as toxicity, irritation, and allergic response and with a reasonable risk/benefit ratio.

Suitably, the composition of the invention comprises a buffer in order to stabilise the pH of the composition, which can also be selected to enhance protein stability. In one embodiment, a buffer is selected to have a pKa close to the pH of the composition; for example acetate is suitably employed as a buffer when the pH of the composition is in the range 4.5-5.5. Histidine is suitably employed as a buffer when the pH of the composition is in the range 5.6-6.5. Alternatively, in another embodiment, the composition of the invention is further stabilised as disclosed in WO2008/084237, which describes a composition comprising a protein and one or more additives, characterised in that the system is substantially free of a conventional buffer, i.e. a compound with a pKa within 1 unit of the pH of the composition at the intended temperature range of storage of the composition. In this embodiment, the pH of the composition is set to a value at which the composition has maximum measurable stability with respect to pH; the one or more additives (displaced buffers) are capable of exchanging protons with the protein and have pKa values at least 1 unit more or less than the pH of the composition at the intended temperature range of storage of the composition. By keeping the protein at a suitable pH, at or near a value at which the measurable stability is maximal, in the absence of a conventional buffer, the storage stability of the protein can be increased substantially. In certain embodiments, storage stability can generally be enhanced further, possibly substantially, by use of additives having pKa between 1 to 5 pH units, preferably between 1 to 3 pH units, most preferably from 1.5 to 2.5 pH units, of the pH of the aqueous composition at the intended temperature range of storage of the composition, The solutions of the invention can further include one or more conventional excipients, such as an inorganic salt, preferably a salt which is a combination of sodium, potassium, calcium, or ammonium, with chloride, sulfate, carbonate, sulfite, nitrate, lactate, succinate, acetate, maleate or lactate; an amino acid, preferably histidine, glycine, arginine or methionine (for example as an anti-oxidant); a sugar or sugar alcohol, preferably trehalose, sucrose, mannitol, raffinose, sorbitol, lactitol, glycerol, or 1,2-propanediol; a surfactant, preferably polysorbate 20, polysorbate 60, polysorbate 80, poloxamer 188 or poloxamer 407; a trace-metal chelating agent, preferably ETDA; a preservative, preferably phenol, m-cresol, benzylalcohol, propylparaben, benzylalkonium chloride or benzethonium chloride. An inorganic salt which is a combination of magnesium with chloride, sulfate, carbonate, sulfite, nitrate, lactate, succinate, acetate, maleate or lactate is also a suitable excipient.

The solutions of the invention optionally comprise a tonicity modifier. Suitable tonicity modifiers are listed above in the background of invention, and can be charged or uncharged chemical species. Typical uncharged tonicity modifiers include sugars such as sucrose, trehalose, glycerol and mannitol. Typical charged tonicity modifiers include charged chemical species, such as arginine or sodium chloride.

In one embodiment, the tonicity of the aqueous solution of antibody protein is adjusted using a charged species such as an inorganic or an organic salt. In one embodiment, the tonicity of the aqueous solution of antibody protein is adjusted using an uncharged species such as a sugar or a sugar alcohol.

The aqueous compositions of the present invention cover a wide range of osmolarity, including hypotonic, isotonic and hypertonic compositions. Preferably, the solutions of the invention are substantially isotonic. Preferred solutions have an osmolarity in the range of about 200 to about 500 mOsm/L. Preferably, the osmolarity is in the range of about 250 to about 350 mOsm/L. More preferably, the osmolarity is about 300 mOsm/L. In one embodiment, the solution is intended for administration to a subject by intramuscular or subcutaneous injection, and the osmolarity of the solution is selected to minimize pain upon injection.

The term "high molecular weight species" as used herein, refers to any component of the protein content which has an apparent molecular weight at least about double the molecular weight of the parent active protein. That is, high molecular weight species are multimeric aggregates of the parent protein. The multimeric aggregates may comprise the parent protein molecules with considerably altered conformation or they may be an assembly of the parent protein units in the native or near-native conformation. The determination of high molecular weight species can be done using methods known in the art, including size exclusion chromatography, electrophoresis, analytical ultracentrifugation/sedimentation velocity, light scattering, dynamic light scattering, static light scattering and field flow fractionation.

Preferably, the composition of the invention comprises no more than 5% (by weight of total protein) high molecular weight species after storage at 40° C. for at least one, two or three months. In one embodiment, the amount of high molecular weight species increases by no more than 5% (by weight of total protein), preferably no more than 3%, after storage at 40° C. for at least one, two or three months. Quantitation of high molecular weight species is as percent by weight of the total protein in the composition.

In preferred embodiments, a composition of the present invention should exhibit an increase in high molecular weight species during storage which is at least 10% lower, preferably at least 25% lower, more preferably at least 50% lower, than a composition lacking the oligomer of ethyleneimine but otherwise identical, following storage under the same conditions and length of time.

In one embodiment, the compositions of the invention are pharmaceutical compositions suitable for administration of a therapeutic antibody protein to a subject in need thereof. Such compositions can be used in a method for administering the therapeutic protein to the subject.

In another embodiment, the invention provides a method for administering a therapeutic antibody protein to a subject in need thereof. The method comprises the step of administering an aqueous solution comprising the antibody protein at a concentration of at least about 10 mg/mL, and an oligomer of ethyleneimine wherein the number of repeating units of ethyleneimine (n) in the oligomer is in the range 2-12. Preferably the composition is administered by intravenous, subcutaneous or intramuscular injection. More preferably the composition is administered by subcutaneous injection.

In preferred embodiments, the concentration of the protein is sufficiently high that the total volume of each administration does not exceed about 2 mL. Preferably, the total volume of each administration does not exceed about 1.5 mL or about 1.0 mL. In one embodiment, the volume of solution of each administration is from about 0.5 to about 2 mL, preferably from about 0.5 to about 1.5 mL.

In another embodiment, the invention provides a packaged pharmaceutical composition suitable for administration to a subject in need thereof. The pharmaceutical composition comprises an aqueous solution comprising a therapeutic antibody protein at a concentration of at least about 10 mg/mL and an oligomer of ethyleneimine wherein the number of repeating units of ethyleneimine (n) in the oligomer is in the range 2-12.

Preferably, the volume of the solution is about 2 mL or less. In one embodiment, the volume of the solution provides an administration volume of about 0.5 to about 2 mL with sufficient overage to accommodate limitations of solution uptake via syringe. In one embodiment, the overage is from about 10% to about 20% of the administration volume. The pharmaceutical composition is preferably packaged in a vial suitable for introduction of a needle for removal of the solution. In one embodiment, the pharmaceutical composition is packaged in a glass vial with a rubber stopper. The packaged pharmaceutical composition can be provided as a kit, further comprising instructions for use and, optionally, a syringe suitable for intramuscular or subcutaneous administration. Alternatively, the packaged pharmaceutical composition can be provided in the form of a pre-filled disposable syringe suitable for intramuscular or subcutaneous administration. A pre-filled auto-injector device would also be suitable for intramuscular or subcutaneous administration.

Percentages of oligomer of ethyleneimine as used herein refer to weight based on free base of oligomer of ethyleneimine (i.e. excluding weight of any counterion).

In another aspect, the present invention provides a compound of Formula V:

X—Y$_1$—[CH$_2$CH$_2$NH]$_n$—R     Formula V wherein, n=2-6; X is selected from the group consisting of polyethylene glycol (e.g. PEG-O— and mPEG-O—), polypropylene glycol (PPG-O—), and a poly-amino acid; Y$_1$ is selected from the group consisting of —(C$_2$-C$_6$)alkyl-C(O)—NH— and (CH$_2$)$_m$K wherein m=3-10 and K represents NH; and R is H or an inert capping group selected from the group consisting of —C$_1$-C$_6$alkyl, —(C$_2$-C$_6$alkyl)-OH and —(C$_2$-C$_6$alkyl)-O—(C$_1$-C$_6$alkyl).

In one embodiment of Formula (V), n is 3-5.

In one embodiment of Formula (V), X has a MW of 500 Da to 5000 Da and is polyethylene glycol (e.g. PEG-O— and mPEG-O—) or polypropylene glycol (PPG-O—), suitably X has a MW of about 2000 Da or about 5000 Da and is mPEG-O—.

In one embodiment of Formula (V), Y$_1$ is —(C$_2$-C$_6$)alkyl-C(O)—NH—, suitably -(C$_2$-C$_4$)alkyl-C(O)—NH—.

In one embodiment of Formula (V), Y$_1$ is (CH$_2$)$_m$K wherein m=3-10, for example m=3 or 4, and K represents NH.

In one embodiment of Formula (V), R is H. In one embodiment of Formula (V), R is —(C$_2$-C$_4$alkyl)-OH.

In one embodiment of Formula (V), n=2-6, X has a MW of 500 Da to 5000 Da, and is polyethylene glycol (e.g. PEG-O— and mPEG-O—) or polypropylene glycol (PPG-O—); Y$_1$ is selected from the group consisting of —(C$_2$-C$_6$)alkyl-C(O)—NH— and (CH$_2$)$_m$K wherein m=3-10 and K represents NH; and R is H or an inert capping group selected from the group consisting of —C$_1$-C$_6$alkyl, —(C$_2$-C$_6$alkyl)-OH and —(C$_2$-C$_6$alkyl)-O—(C$_1$-C$_6$alkyl).

In one embodiment of Formula (V), n=2-6, X is polyethylene glycol (e.g. PEG-O— and/or mPEG-O—); Y$_1$ is selected from the group consisting of —(C$_2$-C$_6$)alkyl-C(O)—NH— and (CH$_2$)$_m$K wherein m=3-4 and K represents NH; and R is H or an inert capping group selected from the group consisting of —C$_1$-C$_6$alkyl, —(C$_2$-C$_6$alkyl)-OH and —(C$_2$-C$_6$alkyl)-O—(C$_1$-C$_6$alkyl).

In one embodiment of Formula (V), n=2-6, X is mPEG-O—; Y$_1$ is selected from the group consisting of —(C$_2$-C$_6$)alkyl-C(O)—NH— and (CH$_2$)$_m$K wherein m=3-4 and K represents NH; and R is H or —(C$_2$-C$_6$alkyl)-OH.

In one embodiment of Formula (V), n=2-6, X is polyethylene glycol (e.g. PEG-O— and mPEG-O—); Y$_1$ is selected from the group consisting of —(C$_2$-C$_6$)alkyl-C(O)—NH— and (CH$_2$)$_m$K wherein m=3-4 and K represents NH; and R is H or —(C$_2$-C$_6$alkyl)-OH; wherein when Y$_1$ is (CH$_2$)$_m$K then R is —(C$_2$-C$_6$alkyl)-OH.

Exemplary compounds of formula (V) include mPEG valerate amido pentaethylenehexamine (e.g. in which the mPEG is 2K mPEG), mPEG valerate amido tetraethylenepentamine (e.g. in which the mPEG is 2K mPEG), mPEG valerate amido triethylenetetramine (e.g. in which the mPEG is 2K mPEG), mPEG propyl triethylenetetramine ethanol (e.g. in which the mPEG is 2K or 5K mPEG) and mPEG propyl pentaethylenehexamine ethanol (e.g. in which the mPEG is 2K or 5K mPEG).

Compounds of formula (V) may be prepared using methods described in the Examples and methods analogous thereto together with methods known to the skilled person.

For example, compounds of Formula (V) wherein Y$_1$ is —(C$_2$-C$_6$)alkyl-C(O)—NH— may be prepared as follows, wherein LG represents a leaving group such as O-succinimide (see for example, synthesis of Compound (I)):

Scheme 1

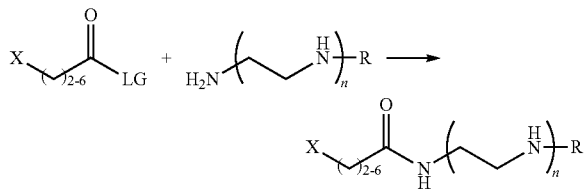

Compounds of Formula (V) wherein Y$_1$ is (CH$_2$)$_m$K wherein K is NH may be prepared as follows via reductive amination:

Scheme 2

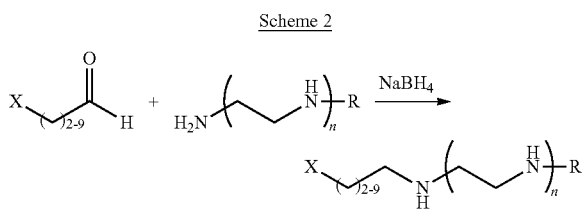

In Schemes 1 and 2 the oligomer of ethyleneimine is pre-functionalised with R before being reacted with the polyethylene glycol-containing compound. It is equally possible to react the un-functionalised oligomer of ethyleneimine (wherein R=H) with the polyethylene glycol-containing compound, followed by subsequent reaction to add capping group R as follows, wherein LG is a suitable leaving group, such as O-succinimide, Cl, Br or I:

Scheme 3

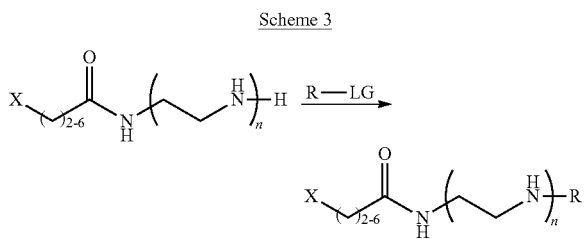

Scheme 3 is an alternative to Scheme 1, however this reverse ordering of steps in which capping group R is added once the oligomer of ethyleneimine and polyethylene glycol-containing group X have been coupled applies equally to Scheme 2.

When R is —($C_2$-$C_6$alkyl)-OH additional steps may be required if the hydroxyl group of R is protected prior to coupling. For example, if group R is protected with an —SiMe$_2$$^t$Bu group (tertbutyldimethylsilyl), once coupled to the oligomer of ethyleneimine the —SiMe$_2$$^t$Bu group must be removed in an extra deprotection step as follows:

Scheme 4

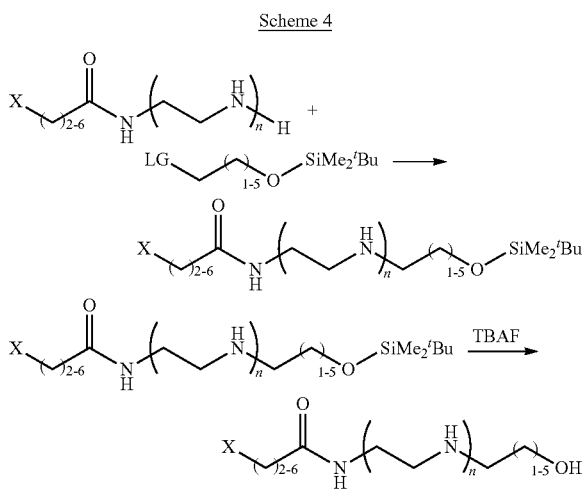

Reagents suitable for the removal of silicon protecting groups such as tertbutyldimethylsilyl include fluorinated reagents, for example tetrabutylammonium fluoride (TBAF) (see for example Step 3 in the synthesis of Compound (2)).

The compounds of Formula (V) above are useful in the solutions, compositions and methods of the invention.

Further aspects of the invention include:

A. An aqueous solution comprising:
  (a) an antibody protein at a concentration of at least about 10 mg/mL, 25 mg/mL, 30 mg/mL, 40 mg/mL, 50 mg/mL, 60 mg/mL, 70 mg/mL, 80 mg/mL, 90 mg/mL or 100 mg/mL, or a range of about 25 mg/mL to about 400 mg/mL (e.g., up to about 350 mg/mL, 300 mg/mL, 250 mg/mL, 200 mg/mL or 175 mg/mL); and
  (a) an oligomer of ethyleneimine of Formula I, Formula II, Formula III, Formula IV, or Formula V as described herein, wherein the number of repeating units of ethyleneimine (n) in the oligomer is in the range 2-12 (or in the range according to the definition of Formula V), and wherein the concentration of the ethyleneimine is about 0.01 to about 10 mg/mL (e.g., from about 0.01 to about 0.1 mg/mL, about 0.1 to about 0.25 mg/mL, about 0.25 to about 1 mg/mL, about 1 to about 2 mg/mL, about 2 to about 5 mg/mL, or about 5 to about 10 mg/mL); and wherein the pH of the aqueous solution is in the range 4 to 8 (e.g. 5.0 to 7.5 or 5.5 to 7.0) and the solution has an osmolarity in the range of about 200 to about 500 mOsm/L.

B. The aqueous solution of aspect A, wherein the solution comprises a buffer providing a pH sufficient to allow dissolution of the protein to the desired concentration and sufficiently low to allow for the protonation of a portion of the basic groups in the oligomer of ethyleneimine.

C. The aqueous solution of aspect A or B, wherein the oligomer of ethyleneimine is derivatised with a chemically inert polymer which is optionally end-capped.

D. The aqueous solution of aspect A, B or C, wherein the concentration of the antibody protein is sufficiently high such that the total volume of each administration dose does not exceed about 2 mL.

E. The aqueous solution of aspect A, B, C or D, wherein the aqueous solution further comprises one or more conventional excipients.

EXAMPLES

Materials

Ethylenediamine (Mw 60 Da), diethylenetriamine (Mw 103 Da), triethylenetetramine (Mw 146 Da), tetraethylenepentamine (Mw 189 Da), pentaethylenehexamine (Mw 232 Da) and PEI800 (Polyethylenimine, ethylenediamine branched, average Mw~800 by LS, average Mn~600 by GPC) were obtained from Sigma-Aldrich. 5K mPEG alcohol (Mw 5000 Da) was obtained from Dr Reddy's CPS. 2K mPEG succinimidyl valerate was obtained from Layson Bio. 5K mPEG propionaldehyde was obtained from Dr Reddy's CPS.

Abbreviations

CPE cytopathic effect
DMEM Dulbecco's Minimum Essential Medium
FBS Foetal Bovine Serum
HEK Human Embryonic Kidney
MDCK Madin-Darby Canine Kidney Epithelial
MTBE methyl tert-butyl ether
mPEG polyethylene glycol polymer capped with methoxy
PEG polyethylene glycol
PEI polyethyleneimine
PPG polypropylene glycol
THF tetrahydrofuran Synthesis of Selected Derivatives of Oligomers of Ethyleneimine The following derivatised oligomers of ethyleneimine were synthesised:

Compound (1) mPEG-O(CH$_2$)$_4$CONH—(CH$_2$CH$_2$NH)$_5$H (=2K mPEG Valerate Amido Pentaethylenehexamine) (Approx. Mw 2331)

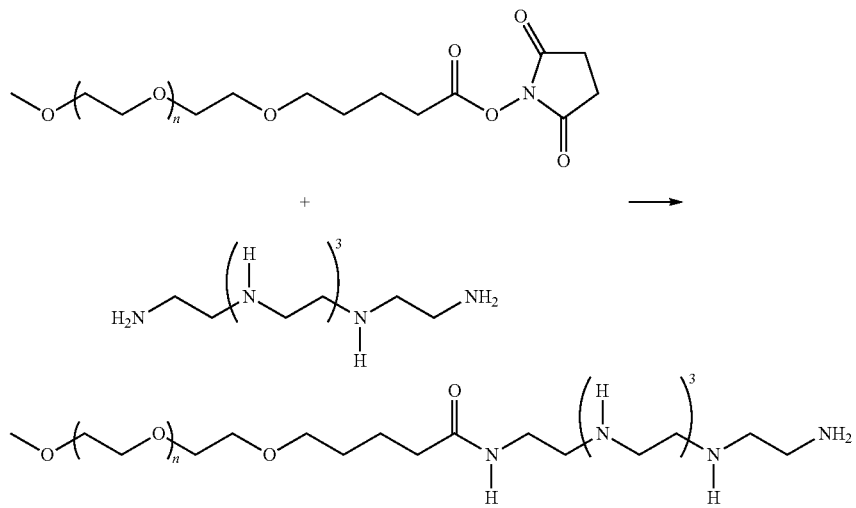

2K mPEG succinimidyl valerate (1.5 g, 0.75 mmol) was dissolved in acetonitrile (45 ml). Pentaethylenehexamine (0.26 g, 1.12 mmol) was also dissolved in acetonitrile (5 ml) and added dropwise to the dissolved mPEG reagent over several minutes. The reaction mixture was then stirred overnight at ambient temperature, after which time an opaque suspension was afforded. The reaction mixture was filtered through Celite© before the mPEG component was precipitated from acetonitrile by addition of methyl tert-butyl ether (MTBE) (300 ml). The suspension was chilled in an ice/water bath prior to filtration through paper, and washed with additional methyl tert-butyl ether (50 ml). The wet product was dried at ambient temperature under reduced pressure for several hours, to afford the title oligomer as a white solid (1.24 g; 83%).

$^1$H NMR (CDCl$_3$, 400 MHz); 3.41-3.84 (m, PEG and m, OCH$_2$CH$_2$CH$_2$CH$_2$CONH), 3.38 (s, OCH$_3$), 2.37-3.36 (m, various CH$_2$), 2.21 (m, CH$_2$CONH), 1.56-1.72 (m, OCH$_2$CH$_2$CH$_2$CH$_2$CONH).

Compound (2) mPEG-O(CH$_2$)$_3$—(NHCH$_2$CH$_2$)$_3$NHCH$_2$CH$_2$OH (=5K mPEG Propyl Triethylenetetramine Ethanol) (Approx. Mw 5247)

Step 1: Mono-Protected Diamine

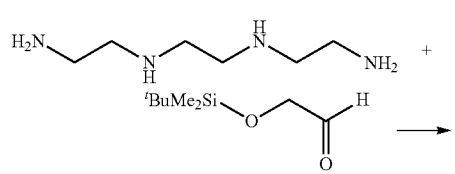

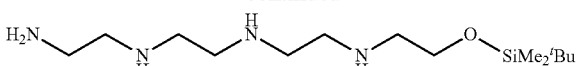

Triethylenetetramine (1.15 g, 7.9 mmol) and (tert-butyldimethylsilyloxy)acetaldehyde (0.7 g, 3.9 mmol, 0.5 equivalents) were combined in methanol (50 ml) and stirred for 1 hour at ambient temperature. After which time sodium borohydride (89 mg, 2.4 mmol, 0.3 equivalents) was added, this afforded a slight effervescence. The reaction mixture was stirred for 15 minutes and then the methanol solvent was removed under reduced pressure. The resultant opaque liquid was dissolved in dichloromethane (50 ml) and washed with water (10 ml) and brine (10 ml). The layers generated were opaque, but separated rapidly. The dichloromethane layer was separated and dried with sodium sulphate, the drying agent removed, and the solvent removed under reduced pressure. This afforded the mono-protected diamine 1.0 g (42% from diamine) as an opaque liquid.

Step 2: Reaction with 5K mPEG-Propionaldehyde

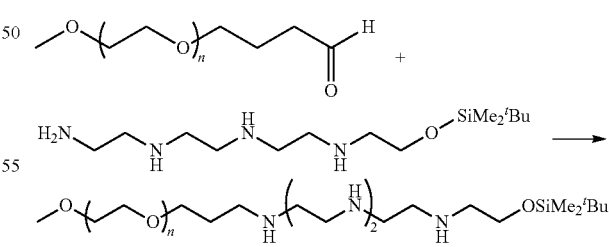

5K mPEG propionaldehyde (5.0 g, 1 mmol) and the mono-protected diamine of Step 1 (1.52 g, 5 mmol, 5 equivalents) were dissolved in methanol (60 ml) and stirred at ambient temperature for 1 hour. Sodium borohydride (0.11 g, 3 mmol, 3 equivalents) was added and the reaction mixture stirred for 15 minutes. The methanol solvent was then removed under reduced pressure, to afford a wet white solid. This was dissolved in dichloromethane (30 ml) and the product was precipitated with MTBE (300 ml) to give the silyl protected product 5.3 g (100%) as a white solid.

Step 3: Deprotection to mPEG Propyl Triethylenetetramine Ethanol

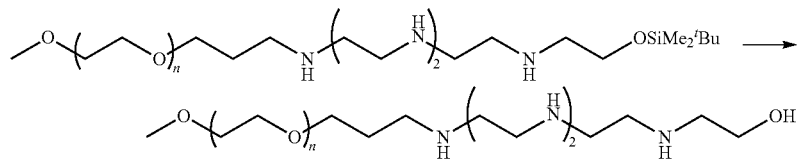

The silyl protected precursor of Step 2 (4.8 g, 0.96 mmol) was dissolved in tetrahydrofuran (THF) (50 ml) by gentle warming in a warm water bath (~40° C.). Tetrabutylammonium fluoride (1.5 ml, 1M solution in THF, 1.5 equivalents) was then added and the reaction mixture stirred at ambient temperature overnight. MTBE (125 ml) was added to the reaction mixture and the precipitate collected by filtration. The wet filter cake was dissolved in dichloromethane (10 ml) and precipitated by the addition of propan-2-ol (250 ml). The precipitation from dichloromethane and propan-2-ol was then repeated and the white solid isolated, dried at 30° C. for 3 hours to afford the title product 2.2 g (45%) as a dense white solid. $^1$H NMR (CDCl$_3$, 400 MHz); 3.43-3.84 (m, PEG, CH$_2$OH and PEGOCH$_2$), 3.38 (s, OCH$_3$), 2.45-2.85 (m, multiple CH$_2$N), 1.72-1.82 (2H, m, PEGCH$_2$CH$_2$CH$_2$NH).

Compound (3) mPEG-O(CH$_2$)$_3$—(NHCH$_2$CH$_2$)$_5$ NHCH$_2$CH$_2$OH (=5K mPEG Propyl Pentaethylenehexamine Ethanol) (Approx. Mw 5333 Da)

Step 1: Mono-Protected Diamine

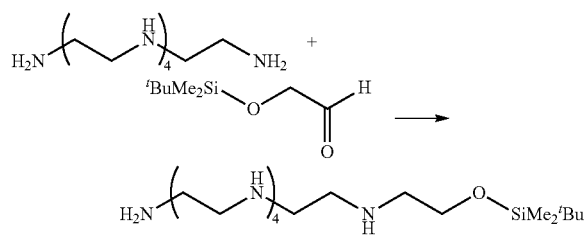

Pentaethylenehexamine (5.3 g, 23.0 mmol) and (tert-butyldimethylsilyloxy)acetaldehyde (2.0 g, 11.5 mmol, 0.5 equivalents) were combined in methanol (100 ml) and stirred for 1 hour at ambient temperature. After which time sodium borohydride (260 mg, 6.9 mmol, 0.3 equivalents) was added, this afforded a slight effervescence. The reaction mixture was stirred for 15 minutes and then the methanol solvent was removed under reduced pressure. The resultant opaque liquid was dissolved in dichloromethane (75 ml) and washed with water (10 ml) and brine (10 ml), twice. The layers generated were opaque, but separated rapidly. The dichloromethane layer once separated was dried with sodium sulphate, the drying agent removed, and the solvent removed under reduced pressure. This afforded the mono-protected diamine 3.0 g (33% from diamine) as an opaque pale yellow liquid.

Step 2: Reaction with 5K mPEG-Propionaldehyde

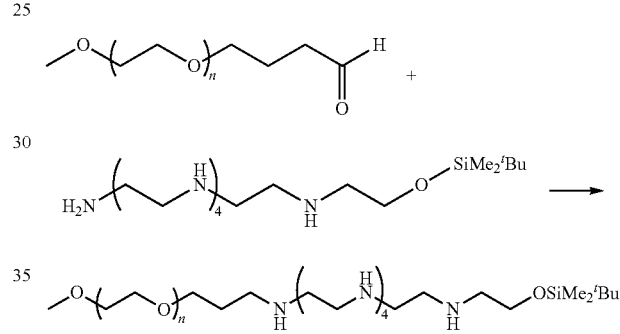

5K mPEG propionaldehyde (5.0 g, 1 mmol) and the mono-protected diamine of Step 1 (1.95 g, 5 mmol, 5 equivalents) were dissolved in methanol (60 ml) and stirred at ambient temperature for 1 hour. Sodium borohydride (0.13 g, 3 mmol, 3 equivalents) was added and the reaction mixture stirred for 15 minutes. The methanol solvent was then removed under reduced pressure, to afford a wet white solid. This was dissolved in dichloromethane (30 ml) and the product was precipitated with MTBE (300 ml) to give the silyl protected product 5.2 g (100%) as a white solid.

Step 3: Deprotection to mPEG Propyl Pentaethylenehexamine Ethanol

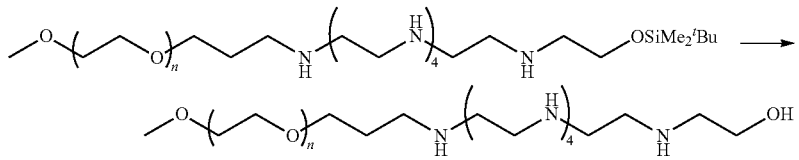

The silyl protected precursor of Step 2 (4.8 g, 0.96 mmol) was dissolved in THF (50 ml) by gentle warming in a warm water bath (~40° C.). Tetrabutylammonium fluoride (1.5 ml, 1M solution in THF, 1.5 equivalents) was then added and the reaction mixture stirred at ambient temperature overnight. MTBE (125 ml) was added to the reaction mixture and the precipitate collected by filtration. The wet filter cake was dissolved in dichloromethane (10 ml) and precipitated by the addition of propan-2-ol (250 ml). The precipitation from dichloromethane and propan-2-ol was then repeated and the white solid isolated, dried at 30° C. for 3 hours to afford the title product 3.1 g (65%) as a dense white solid. $^1$H NMR (CDCl$_3$, 400 MHz); 3.44-3.85 (m, PEG, CH$_2$OH and PEGOCH$_2$), 3.38 (s, OCH$_3$), 2.45-2.83 (m, multiple CH$_2$N), 1.73-1.82 (2H, m, PEGCH$_2$CH$_2$CH$_2$NH).

The following compounds were synthesised as reference materials:

Compound (4) mPEG-O(CH$_2$)$_4$CONH-(PEI800) (=2K mPEG Valerate PEI800) (Approx. Mw 2900 Da)

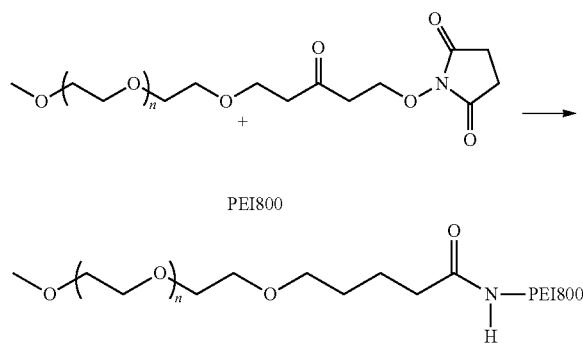

PEI800 (0.48 g, 0.6 mmol) was dissolved in dichloromethane (90 ml) to form an opaque solution. 2K mPEG succinimidyl valerate (1.5 g, 0.75 mmol) was then added in small portions as a solid over several minutes generating a clear solution. The reaction mixture was then stirred overnight at ambient temperature, after which time an opaque suspension was afforded. The extraneous solid was removed by filtration through Celite© before approximately two thirds of the dichloromethane was removed under reduced pressure. The resultant concentrate was then mixed with methyl tert-butyl ether MTBE (300 ml) and chilled in an ice/water bath to obtain precipitation of the product. This was collected by filtration through paper, washed with MTBE (50 ml) and dried at ambient temperature under reduced pressure, for several hours. The title product was afforded as a white solid (1.50 g, 89%).

$^1$H NMR (CDCl$_3$, 400 MHz); 3.41-3.84 (m, PEG and m, OCH$_2$CH$_2$CH$_2$CH$_2$CONH), 3.38 (s, OCH$_3$), 2.43-3.36 (m, various CH$_2$), 2.21 (m, CH$_2$CONH), 1.53-1.74 (m, OCH$_2$CH$_2$CH$_2$CH$_2$CONH).

Compound (5) mPEG-O(CH$_2$)$_3$—NHCH$_2$CH$_2$NHCH$_2$CH$_2$OH (=5K mPEG Propyl-N-(hydroxyethyl)ethylenediamine) (Approx. Mw 5161 Da)

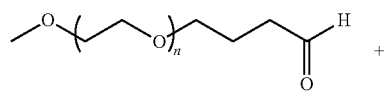

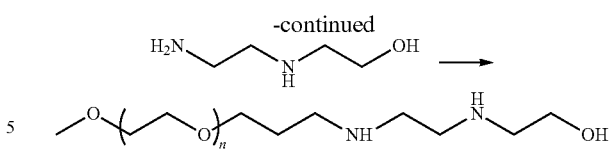

5K mPEG propionaldehyde (2 g, 0.4 mmol) was dissolved in methanol (20 ml) by warming to approximately 40° C. in a water bath. Upon dissolution the mPEG solution was returned to ambient temperature and N-(2-hydroxyethyl)ethylenediamine (0.125 g, 1.2 mmol, 3 equivalents) added. The amine, aldehyde mixture was allowed to stir for 15 minutes prior to the addition of sodium borohydride (45 mg, 1.2 mmol, 3 equivalents), which afforded a slight effervescence. The reaction mixture was stirred at ambient for 1 hour, and then the PEG component was precipitated with MTBE (150 ml), and collected by filtration. The wet filter cake was washed with MTBE (50 ml) and then dried under reduced pressure to afford the title compound (1.86 g, 93%) as a white solid. $^1$H NMR (CDCl$_3$, 400 MHz); 3.43-3.84 (m, PEG, CH$_2$OH and PEGOCH$_2$), 3.38 (s, OCH$_3$), 2.52-2.80 (m, multiple CH$_2$N), 1.72-1.82 (m, PEGCH$_2$CH$_2$CH$_2$NH).

Formulation Preparation and Stability Testing

Formulations of protein therapeutics, rituximab and certolizumab pegol, were prepared either in the absence or in the presence of various oligomers of ethyleneimine. The following products were used as the starting material: MabThera® (rituximab) and Cimzia® (certolizumab pegol). The compositions of the two products are as follows:

MabThera®:
 rituximab (10 mg/ml)
 sodium citrate dihydrate (7.35 mg/ml)
 polysorbate 80 (0.7 mg/ml)
 sodium chloride (9.0 mg/ml)
 pH is approximately 6.5
 Source: EMA Scientific discussion on MabThera® (http://www.ema.europa.eu/docs/en_GB/document_library/EPAR_-_Scientific_Discussion/human/000165/WC500025817.pdf)

Cimzia®:
 certolizumab pegol (200 mg/ml)
 sodium acetate (1.36 mg/ml)
 sodium chloride (7.31 mg/ml)
 pH is approximately 4.7
 Source: RxList (http://www.rxlist.com/script/main/hp.asp)

In order to prepare the formulations for testing, it was necessary to remove the original excipients and replace them with the selected excipients. The following procedure was used to prepare the formulations for testing: Original compositions were removed from the manufacturer's container and dialysed in 3.5 kDa cut-off dialysis cassettes (Thermo Pierce) at 2-8° C., using three changes for a minimum of 4 hours in each, including one overnight incubation. The protein was then concentrated to 133.3 mg/ml (rituximab, Examples 1-4), 187 mg/ml (rituximab, Example 5), or 150 mg/ml (certolizumab pegol, Example 6) using Amicon centrifugal concentrators with MWCO 50 kDa (rituximab) or 30 kDa (certolizumab pegol).

The background solutions, containing the new excipients and adjusted to the required pH, were added to the dialysed proteins to achieve the required concentration of excipients and the protein in the final composition. The formulated samples were placed into storage at 40° C. or at 5° C., and stability was tested after a given period of time. The stability of the proteins was tested in compositions containing oligomers of ethyleneimine and compared to a 'Control formulation' with identical background in the absence of the oligomers. To allow further comparison, an 'Original formulation' was prepared having an identical composition of excipients as that of the original product (i.e. MabThera® in the case of rituximab and Cimzia® in the case of certolizumab pegol) but with a particular concentration of protein, as specified in each Example (e.g. in Example 1, the Original formulation contains 100 mg/ml of rituximab).

Methods of Assessing Aggregation

Aggregation in the aqueous protein compositions can be assessed by:

(a) Visual Assessment

Vials are placed in a suitable location with a suitably selected contrasting background, and under sufficient and appropriate illumination to highlight any potential or detected visual deviations. A control (or freshly prepared material) is placed alongside for direct comparison. Solutions are classed as clear if there are no visual imperfections; as cloudy if there is a significant change in the opacity of the material; and if there are insoluble fractions, or if particles are visible towards the bottom of the vial, a precipitate is deemed to have been formed.

(b) Size Exclusion Chromatography (SEC)

The amount of high molecular weight species is measured using a 300×7.8 mm S3000 (or equivalent) size-exclusion column with a guard column. The mobile phase is potassium phosphate pH 6.5, with a flow rate of 0.4 ml/min, injection volume of 1 μl and detected at 210 and 280 nm. The results are expressed as % high molecular species (HMWS), i.e. sum of all peak areas corresponding to aggregated protein over the sum of all protein-related peaks on the chromatogram. A small time-point to time-point variability can be observed in terms of absolute values of % HMWS, for example due to repeated size-exclusion column use. However, within a given time-point the samples are tested using the column in the same condition, so the values generated within the time-point represent a very good indication of the relative stability of the protein in the compositions tested.

Example 1: Rituximab—Demonstration of Aggregation Control in the Presence of Tetraethylenepentamine and Pentaethylenehexamine Rituximab was formulated at 100 mg/ml in the following background solution: EDTA (0.2 mM), methionine (1 mM), histidine (10 mM). The pH was adjusted to 6.5. The effects of oligomers of ethyleneimine (i) tetraethylenepentamine pentahydrochloride (n=4) and (ii) pentaethylenehexamine (n=5) on the increase in aggregation in the presence of trehalose at 40° C. and 5° C. are shown in Tables 1 and 2 respectively. In all background solutions the presence of oligomers of ethyleneimine (i) and (ii) was found to reduce considerably the rate of formation of HMWS. In addition, at 40° C., precipitation was observed after 8 weeks in the control formulations not containing an oligomer of ethyleneimine.

TABLE 1

The rate of aggregation in formulations of rituximab at 40° C.

| Trehalose* (mM) | Tetraethylenepentamine** (mg/ml) | Pentaethylenehexamine (mg/ml) | pH | % HMWS $T_0$ | % HMWS 8 weeks | Visual (8 weeks) |
|---|---|---|---|---|---|---|
| 200 | | | 6.5 | 1.49 | 2.82 | Clear |
| 200 | 0.1 | | 6.5 | 1.40 | 1.79 | Clear |
| 200 | 0.5 | | 6.5 | 1.44 | 1.85 | Clear |
| 200 | 2.5 | | 6.5 | 1.40 | 1.45 | Clear |
| 200 | | 0.2 | 6.5 | 1.42 | 1.89 | Clear |
| 200 | | 1.0 | 6.5 | 1.40 | 1.24 | Clear |
| 200 | | 5.0 | 6.5 | 1.41 | 1.29 | Clear |
| Original formulation, 154 mM NaCl, 25 mM Citrate, 700 mg/l Tween 80 | | | 6.5 | 1.55 | 3.22 | Clear, ppt at bottom |

*and EDTA (0.2 mM), methionine (1 mM) and histidine (10 mM)
**as pentahydrochloride salt (concentration in column based on weight of base)

TABLE 2

The rate of aggregation in formulations of rituximab at 5° C.

| Trehalose* (mM*) | Tetraethylenepentamine** (mg/ml) | Pentaethylenehexamine (mg/ml) | pH | % HMWS $T_0$ | % HMWS 8 weeks | Visual (8 weeks) |
|---|---|---|---|---|---|---|
| 200 | | | 6.5 | 1.49 | 1.25 | Clear |
| 200 | 0.1 | | 6.5 | 1.40 | 1.23 | Clear |
| 200 | 0.5 | | 6.5 | 1.44 | 1.22 | Clear |
| 200 | 2.5 | | 6.5 | 1.40 | 1.21 | Clear |
| 200 | | 0.2 | 6.5 | 1.42 | 1.22 | Clear |
| 200 | | 1.0 | 6.5 | 1.40 | 1.24 | Clear |
| 200 | | 5.0 | 6.5 | 1.41 | 1.07 | Clear |
| Original formulation, 154 mM NaCl, 25 mM Citrate, 700 mg/l Tween 80 | | | 6.5 | 1.55 | 1.28 | Clear |

*and EDTA (0.2 mM), methionine (1 mM) and histidine (10 mM)
**as pentahydrochloride salt (concentration in column based on weight of base)

Example 2: Rituximab—Further Investigation of Aggregation Control in the Presence of Various Oligomeric and Polymeric Additives Rituximab is formulated at 100 mg/ml in the following background solution: EDTA (0.2 mM), Methionine (1 mM), Histidine (10 mM). The pH is adjusted to 6.5.

The following monomeric, oligomeric and polymeric additives can be tested:
(a) 2K mPEG Valerate Amido Pentaethylenehexamine [compound (1)]
(b) 2K mPEG valerate PEI800 [compound (4)]; control
(c) Ethylenediamine; control
(d) Diethylenetriamine
(e) Triethylenetetramine
(f) Tetraethylenepentamine
(g) Pentaethylenehexamine

TABLE 3

| Arginine (mM) | Trehalose (mM) | (a) (mg/ml) | (b) (mg/ml) | (c) (mg/ml) | (d) (mg/ml) | (e) (mg/ml) | (f) (mg/ml) | (g) (mg/ml) | pH |
|---|---|---|---|---|---|---|---|---|---|
| 80 | | | | | | | | | 6.5 |
| | 200 | | | | | | | | 6.5 |
| | 200 | 0.2 | | | | | | | 6.5 |
| | 200 | 1 | | | | | | | 6.5 |
| | 200 | 5 | | | | | | | 6.5 |
| | 200 | | 0.2 | | | | | | 6.5 |
| | 200 | | 1 | | | | | | 6.5 |
| | 200 | | 5 | | | | | | 6.5 |
| | 200 | | | 0.2 | | | | | 6.5 |
| | 200 | | | 1 | | | | | 6.5 |
| | 200 | | | 5 | | | | | 6.5 |
| | 200 | | | | 0.2 | | | | 6.5 |
| | 200 | | | | 1 | | | | 6.5 |
| | 200 | | | | 5 | | | | 6.5 |
| | 200 | | | | | 0.2 | | | 6.5 |
| | 200 | | | | | 1 | | | 6.5 |
| | 200 | | | | | 5 | | | 6.5 |
| | 200 | | | | | | 0.2 | | 6.5 |
| | 200 | | | | | | 1 | | 6.5 |
| | 200 | | | | | | 5 | | 6.5 |
| | 200 | | | | | | | 0.15 | 6.5 |
| | 200 | | | | | | | 1.5 | 6.5 |
| | 200 | | | | | | | 8 | 6.5 |
| | 200 | | | | | | | 16 | 6.5 |
| Original formulation, 154 mM NaCl, 25 mM Citrate, 700 mg/l Tween 80 | | | | | | | | | 6.5 | found to be lower than in the Original formulation, which also showed signs of precipitation after 8 weeks.

TABLE 4

The rate of aggregation in formulations of rituximab at 40° C.

| Arginine (mM) | Tetraethylene-pentamine (mg/ml) | Pentaethylene-hexamine (mg/ml) | % HMWS 0 weeks | % HMWS 12 weeks |
|---|---|---|---|---|
| 80 | | | 1.47 | 2.57 |
| 80 | 0.1 | | 1.58 | 2.08 |
| 80 | 0.5 | | 1.53 | 1.89 |
| 80 | 2.5 | | 1.47 | 0.85 |
| 80 | | 0.2 | 1.42 | 1.92 |
| 80 | | 1.0 | 1.57 | 1.62 |
| 80 | | 5.0 | 1.36 | 0.83 |

Example 3: Rituximab—Demonstration of Aggregation Control in the Presence of Tetraethylenepentamine and Pentaethylenehexamine, in Alternative Background Solution Containing Arginine Rituximab was formulated at 100 mg/ml in the following background solution: EDTA (0.2 mM), methionine (1 mM), histidine (10 mM), in the presence of arginine (80 mM) as a tonicity modifier. The pH of all formulations was adjusted to 6.5. For comparison, the formulation of commercial liquid rituximab product ('Original formulation' also with rituximab at 100 mg/ml) was also included. The effects of oligomers of ethyleneimine (i) tetraethylenepentamine pentahydrochloride (n=4) and (ii) pentaethylenehexamine (n=5) on the increase in aggregation at 40° C. is shown in Table 4. In all background solutions the presence of oligomers of ethyleneimine (i) and (ii) was found to reduce considerably the rate of formation of HMWS compared with the background solutions not containing an oligomer of ethyleneimine. In addition, the rate of formation of HMWS at 40° C. in the presence of an oligomer of ethyleneimine was TABLE 4-continued The rate of aggregation in formulations of rituximab at 40° C.

| Arginine (mM) | Tetraethylene-pentamine (mg/ml) | Pentaethylene-hexamine (mg/ml) | % HMWS 0 weeks | % HMWS 12 weeks |
|---|---|---|---|---|
| Original formulation: Rituximab (100 mg/ml), sodium citrate dihydrate (7.35 mg/ml), polysorbate 80 (0.7 mg/ml), sodium chloride (9.0 mg/ml), pH 6.5 | | | 1.55 | 3.22 |

Example 4: Rituximab—Demonstration of Aggregation Control by Various Oligomers of Ethyleneimine Rituximab was formulated at 100 mg/ml in the following background solution: EDTA (0.2 mM), methionine (1 mM), histidine (10 mM) and trehalose (200 mM). The pH was adjusted to 6.5. The effects of the following additives on the increase in aggregation in the presence at 40° C. are shown in Table 5.

(a) 2K mPEG Valerate Amido Pentaethylenehexamine [Compound (1)]
(b) Ethylenediamine (reference)
(c) Diethylenetriamine
(d) Triethylenetetramine
(e) Pentaethylenehexamine
(f) 2K mPEG valerate PEI800 [Compound (4)]

The results are expressed in terms of % high molecular species (HMWS) measured by SEC. The following observations were made: in all background solutions the presence of oligomers of ethyleneimine (c), (d) and (e) was found to considerably reduce the rate of formation of HMWS in a dose dependent manner compared with the background formulation not containing an oligomer of ethylene imine; the use of the PEGylated oligomer of ethyleneimine (a) also achieves a stabilisation effect and on a molar basis appears as effective as (c), (d) and (e); the rate of aggregation in the presence of the oligomers of ethyleneimine (a), (c), (d) and (e) was in all cases lower when compared with the formulation of commercial liquid rituximab product ('Original formulation'); another comparator formulation containing ethylenediamine (b) was less effective in reducing the formation of HMWS; another comparator formulation containing 2K mPEG valerate PEI800 (f) reduced the rate of formation of HMWS in a dose dependent manner, but additive (f) can be expected to have a less favourable toxicity profile to additives (a), (c), (d) and (e).

Example 5: Rituximab—Demonstration of Aggregation Control at Higher Concentration by Both PEGylated and Non-PEGylated Oligomers of Ethyleneimine Rituximab was formulated at 140 mg/ml in the following background solution: EDTA (0.2 mM), methionine (1 mM), histidine (10 mM) and trehalose (200 mM). The pH was adjusted to 6.5. The effect of the following additives on the rate of aggregation was investigated:
(a) 5K mPEG Propyl Triethylenetetramine Ethanol [Compound (2)]
(b) 5K mPEG Propyl Pentaethylenehexamine Ethanol [Compound (3)]
(c) 5k mPEG alcohol
(d) Diethylenetriamine
(e) Triethylenetetramine
(f) Pentaethylenehexamine Additive (c) was added to allow a better understanding of the effect of PEGylation of selected oligomers of ethyleneimine.

Figure 1B:
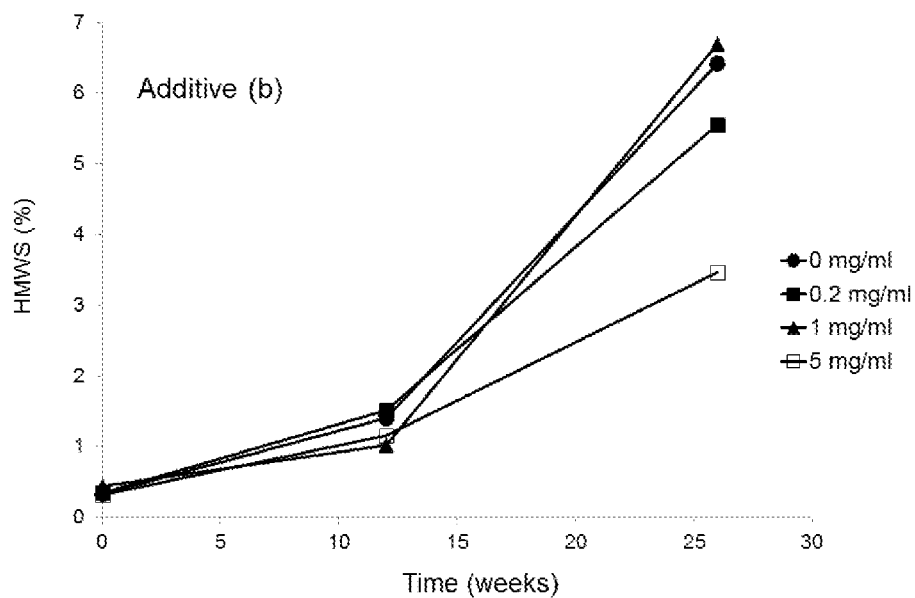
Figure 1C:
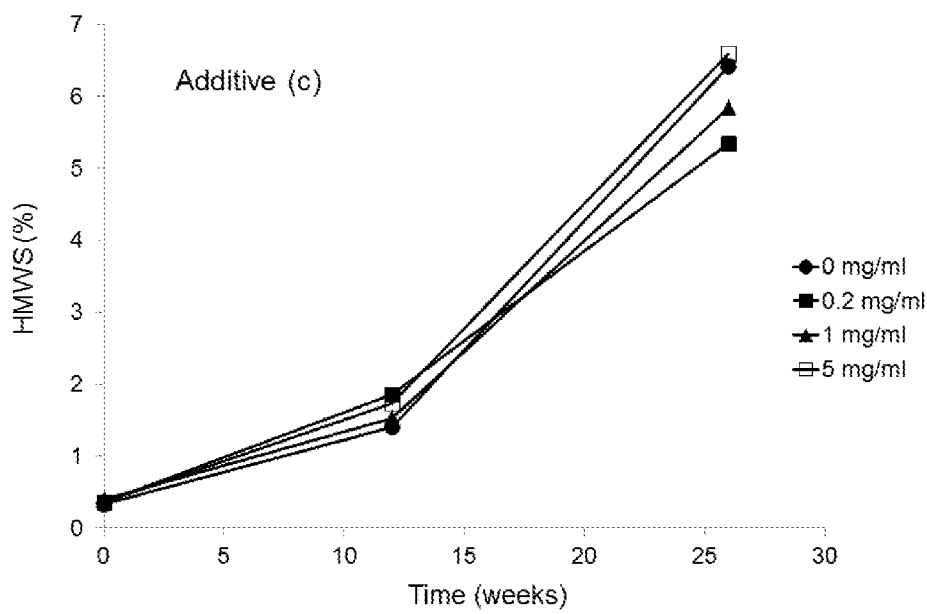
Figure 1D:
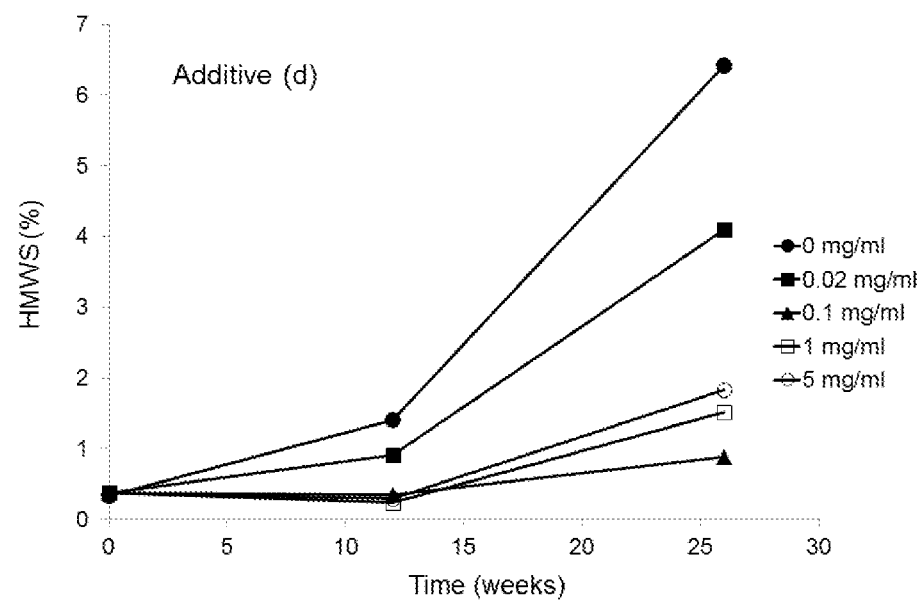
Figure 1E:
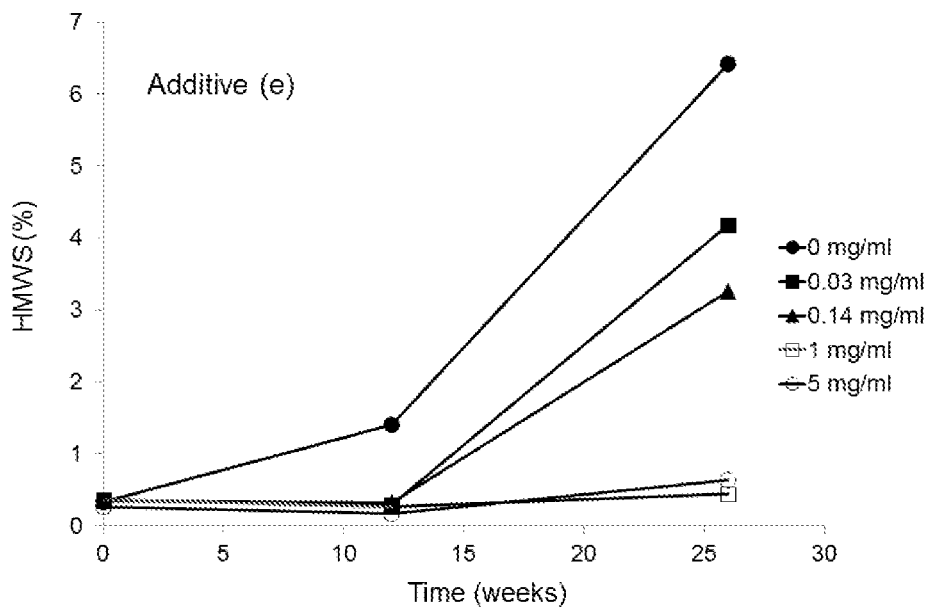
Figure 1F:
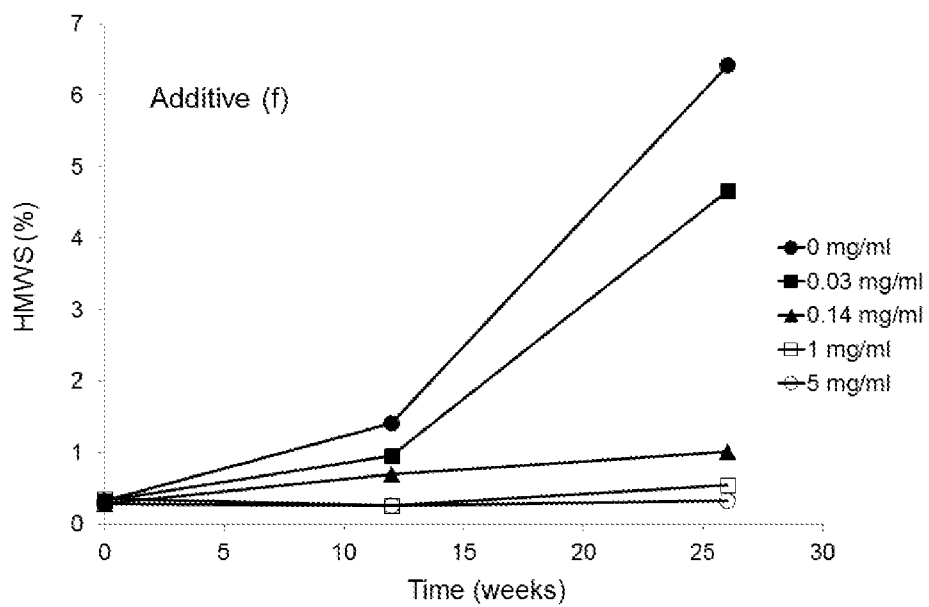

The effect of the oligomers of ethyleneimine on the rate of aggregation of rituximab at 40° C. is shown in Table 6. The results are expressed in terms of % high molecular species (HMWS) measured by SEC. The same results are also shown in FIGS. 1A-1F. A reduction in the rate of aggregation was observed in the presence of 5K mPEG Propyl Triethylenetetramine Ethanol (a) and 5K mPEG Propyl Pentaethylenehexamine Ethanol (b) (FIGS. 1A and 1B). The effect was dose-dependent, and in the case of 5k mPEG pentaethylenehexamine (b) the effect was only observed at 5 mg/ml. In contrast, the 5k mPEG alcohol (c) alone had only marginal effect on the rate of aggregation (FIG. 1C). Non-PEGylated oligomers of ethyleneimine (d), (e) and (f) showed a considerable, dose-dependent reduction in the aggregation rate of rituximab (FIGS. 1D-1F).

TABLE 5

The rate of aggregation in formulations of rituximab after 16 weeks at 40° C.

| (a) (mg/ml)/mM | (b) (mg/ml)/mM | (c) (mg/ml)/mM | (d) (mg/ml)/mM | (e) (mg/ml)/mM | (f) (mg/ml)/mM | % HWMS 0 weeks | % HMWS 16 weeks |
|---|---|---|---|---|---|---|---|
|  |  |  |  |  |  | 0.69 | 3.21 |
| 0.2/0.086 |  |  |  |  |  | 0.73 | 2.47 |
| 1/0.43 |  |  |  |  |  | 0.73 | 1.18 |
| 5/2.1 |  |  |  |  |  | 0.70 | 0.88 |
|  | 0.2/3.3 |  |  |  |  | 0.49 | 2.44 |
|  | 1/17 |  |  |  |  | 0.72 | 2.27 |
|  | 5/83 |  |  |  |  | 0.78 | 2.08 |
|  |  | 0.2/1.9 |  |  |  | 0.81 | 0.94 |
|  |  | 1/9.7 |  |  |  | 0.70 | 0.70 |
|  |  | 5/49 |  |  |  | 0.79 | 0.67 |
|  |  |  | 0.2/1.4 |  |  | 0.74 | 0.81 |
|  |  |  | 1/6.8 |  |  | 0.84 | 0.56 |
|  |  |  | 5/34 |  |  | 0.74 | 0.51 |
|  |  |  |  | 0.15/0.65 |  | 0.59 | 1.28 |
|  |  |  |  | 1.5/6.5 |  | 0.67 | 0.24 |
|  |  |  |  | 8/34 |  | 0.52 | 0.17 |
|  |  |  |  | 16/69 |  | 0.73 | 0.16 |
|  |  |  |  |  | 0.2/0.069 | 0.69 | 2.57 |
|  |  |  |  |  | 1/0.34 | 0.79 | 1.06 |
|  |  |  |  |  | 5/1.7 | 0.69 | 0.93 |
| Original formulation: Rituximab (100 mg/ml), sodium citrate dihydrate (7.35 mg/ml), polysorbate 80 (0.7 mg/ml), sodium chloride (9.0 mg/ml), pH 6.5 | | | | | | 0.75 | 3.40 |

TABLE 6

Effect of PEGylated and non-PEGylated oligomers of ethyleneimine and 5k mPEG alcohol on the rate of aggregation in formulations of rituximab at 40° C.

| (a) (mg/ml)/ mM | (b) (mg/ml)/ mM | (c) (mg/ml)/ mM | (d) (mg/ml)/ mM | (e) (mg/ml)/ mM | (f) (mg/ml)/ mM | % HMWS 0 weeks | % HMWS 12 weeks | % HMWS 26 weeks |
|---|---|---|---|---|---|---|---|---|
| | | | | | | 0.33 | 1.41 | 6.42 |
| 0.2/0.038 | | | | | | 0.25 | 1.31 | 4.79 |
| 1/0.19 | | | | | | 0.40 | 1.17 | 4.44 |
| 5/0.95 | | | | | | 0.35 | 0.97 | 3.60 |
| | 0.2/0.038 | | | | | 0.35 | 1.51 | 5.55 |
| | 1/0.19 | | | | | 0.45 | 1.02 | 6.69 |
| | 5/0.94 | | | | | 0.32 | 1.16 | 3.47 |
| | | 0.2/0.040 | | | | 0.36 | 1.86 | 5.34 |
| | | 1/0.20 | | | | 0.40 | 1.53 | 5.84 |
| | | 5/1.00 | | | | 0.36 | 1.73 | 6.60 |
| | | | 0.02/0.19 | | | 0.37 | 0.91 | 4.09 |
| | | | 0.1/0.97 | | | 0.38 | 0.35 | 0.89 |
| | | | 1/9.7 | | | 0.38 | 0.24 | 1.51 |
| | | | 5/49 | | | 0.37 | 0.29 | 1.83 |
| | | | | 0.03/0.21 | | 0.36 | 0.29 | 4.18 |
| | | | | 0.14/0.96 | | 0.35 | 0.32 | 3.26 |
| | | | | 1/6.8 | | 0.36 | 0.27 | 0.45 |
| | | | | 5/34 | | 0.26 | 0.17 | 0.64 |
| | | | | | 0.04/0.17 | 0.33 | 0.96 | 4.66 |
| | | | | | 0.22/0.95 | 0.28 | 0.69 | 1.01 |
| | | | | | 1/4.3 | 0.36 | 0.26 | 0.54 |
| | | | | | 5/22 | 0.29 | 0.26 | 0.32 |
| Original formulation: Rituximab (140 mg/ml), sodium citrate dihydrate (7.35 mg/ml), polysorbate 80 (0.7 mg/ml), sodium chloride (9.0 mg/ml), pH 6.5 | | | | | | 0.31 | 1.23 | 3.34 |

Example 6: Certolizumab Pegol—Demonstration of Aggregation Control in the Presence of PEGylated and Non-PEGylated Oligomers of Ethyleneimine Certolizumab pegol was formulated at 100 mg/ml in histidine buffer (10 mM, pH 6.0) in the presence of either NaCl (150 mM) or 1,2-propandiol (200 mM) as tonicity modifiers. The effects of oligomers of ethyleneimine (b)-(e) on the rate of aggregation at 40° C. are shown in Table 7 (150 mM NaCl tonicity modifier) and Table 8 (200 mM 1,2-propanediol tonicity modifier).

The following additives were tested:
(a) 5k mPEG alcohol
(b) Pentaethylenehexamine
(c) 2K mPEG Valerate Amido Pentaethylenehexamine [Compound (1)]
(d) Triethylenetetramine
(e) 5K mPEG Propyl Triethylenetetramine Ethanol [Compound (2)]

The results are expressed in terms of % high molecular species (HMWS) measured by SEC. Oligomers of ethyleneimine (b)-(e), both PEGylated and non-PEGylated, were found to reduce the rate of formation of HMWS, especially oligomers (b), (c) and (d).; With the exception of (e) in the composition containing 1,2-propanediol (Table 8), this effect increased with dose. It was also shown that the rate of HMWS formation was considerably lower in the presence of the oligomers of ethyleneimine compared with the formulation of the commercial liquid product of Certolizumab pegol ('Original formulation'). Additionally, another comparator formulation containing mPEG alcohol (a) was shown to be ineffective in reducing the rate of HMWS formation.

TABLE 7

The rate of aggregation in formulations of Certolizumab pegol at 40° C. in compositions containing NaCl.

| NaCl (mM) | (a) (mg/ml)/ mM | (b) (mg/ml)/ mM | (c) (mg/ml)/ mM | (d) (mg/ml)/ mM | (e) (mg/ml)/ mM | % HMWS 0 weeks | % HMWS 8 weeks |
|---|---|---|---|---|---|---|---|
| 150 | 1/0.20 | | | | | 0.70 | 3.15 |
| 150 | | 1/4.3 | | | | 0.53 | 1.72 |
| 150 | | 3/13 | | | | 0.45 | 1.21 |
| 150 | | | 3/1.3 | | | 0.56 | 1.86 |
| 150 | | | 10.1/4.3 | | | 0.59 | 1.60 |
| 150 | | | | 1/6.9 | | 0.63 | 1.51 |
| 150 | | | | 3/21 | | 0.49 | 1.02 |
| 150 | | | | | 3/0.57 | 0.66 | 3.32 |
| 150 | | | | | 35.9/6.8 | 0.79 | 2.39 |
| Original formulation: Certolizumab pegol (100 mg/ml), sodium acetate (1.36 mg/ml), sodium chloride (7.31 mg/ml), pH 4.7 | | | | | | 0.53 | 3.06 |

TABLE 8

The rate of aggregation in formulations of Certolizumab pegol at 40° C. in compositions containing 1,2-propanediol.

| 1,2-propanediol (mM) | (a) (mg/ml)/mM | (b) (mg/ml)/mM | (c) (mg/ml)/mM | (d) (mg/ml)/mM | (e) (mg/ml)/mM | % HMWS 0 weeks | % HMWS 8 weeks |
|---|---|---|---|---|---|---|---|
| 200 | 1/0.20 | | | | | 0.55 | 2.92 |
| 200 | | 1/4.3 | | | | 0.47 | 1.35 |
| 200 | | 3/13 | | | | 0.45 | 1.03 |
| 200 | | | 3/1.3 | | | 0.55 | 1.74 |
| 200 | | | 10.1/4.3 | | | 0.56 | 1.41 |
| 200 | | | | 1/6.9 | | 0.55 | 1.02 |
| 200 | | | | 3/21 | | 0.49 | 0.85 |
| 200 | | | | | 3/0.57 | 0.64 | 2.02 |
| 200 | | | | | 35.9/6.8 | 0.81 | 2.47 |
| Original formulation: Certolizumab pegol (100 mg/ml), sodium acetate (1.36 mg/ml), sodium chloride (7.31 mg/ml), pH 4.7 | | | | | | 0.53 | 3.06 |

Method of Assessing Cytotoxicity

Example 7: Determining the Effect of Size of PEI on the Cytotoxic Effect on HEK 293 and Vero Cells Cell lines Human Embryonic Kidney (HEK) 293, obtained from University of Birmingham, and Vero, obtained from ECACC (The European Collection of Cell Cultures), were subcultured and used to set up 96 well plates at a concentration of $1 \times 10^4$ cells/cm$^2$ in Dulbecco's Minimum Essential Medium (DMEM)+2% Foetal Bovine Serum (FBS)+4 mM L-Glutamine. The cells were incubated for 24 hours at 37° C. to become confluent. After 24 hours various PEI's of molecular weight between about 800 Da and about 50,000 Da were prepared to a stock concentration of 5 mg/mL and had their pH adjusted to 7: (molecular weights 600, 1800, 10,000 and 50-100,000). The stock was then diluted in DMEM+2% FBS+4 mM L-Glutamine to the following concentrations: 2.5 mg/mL, 1.25 mg/mL, 600 ug/mL, 300 ug/mL, 150 ug/mL, 75 ug/mL, 25 ug/mL, 10 ug/mL and 5 ug/mL. Following the dilution step 100 µL of all of the concentrations, including the stock concentration, were added to 8 wells/plate, giving 8 replicates/concentration. The plates were incubated at 37° C. for 72 hours before being screened for cytopathic effect (CPE), as shown in FIG. 2. As discussed above, FIG. 2 clearly demonstrates that as the PEI decreases in size, so does its cytotoxic effect.

The cytotoxic effect of oligomers of ethyleneimine of the present invention can be tested by substantially the same method.

Example 8: Effect of Size of Ethyleneimine Oligomer on Cytotoxic Effect Using Vero and MDCK Cells Vero cells and Madin-Darby Canine Kidney Epithelial (MDCK) cells were obtained from ECACC (The European Collection of Cell Cultures, Health Protection Agency, Porton Down, Salisbury, SP4 0JG). The cells were subcultured and used to set up 96 well plates at a concentration of $1 \times 10^4$ cells/cm$^2$ in Dulbecco's Minimum Essential Medium (DMEM)+2% Foetal Bovine Serum (FBS)+4 mM L-Glutamine. The cells were incubated for 24 hours at 37° C. to become confluent. After 24 hours, various ethyleneimine oligomers and polymers (i.e. PEI's) were prepared to a stock concentration of 5 mg/mL and had their pH adjusted to 7. Oligomers and polymers of the following molecular weight were tested: 102, 145, 188, 231, 800, 1800, 10,000 and 50-100,000 Da. The stock solutions were then diluted in DMEM+2% FBS+4 mM L-Glutamine to the following concentrations: 2.5 mg/mL, 1.25 mg/mL, 600 µg/mL, 300 µg/mL, 150 µg/mL, 75 µg/mL, 25 µg/mL, 10 µg/mL and 5 µg/mL. Following the dilution step 100 µL of each the sample at each concentration were added to 8 wells on a plate, giving 8 replicates per concentration. The plates were incubated at 37° C. for 72 hours before being screened for cell inhibition and cytopathic effect (CPE). FIG. 3 demonstrates that the size of ethyleneimine oligomer or polymer is directly related to the cytotoxic effect in Vero cells; the smaller the size the smaller the cytotoxic effect as determined by the concentration of ethyleneimine oligomer or polymer required for the cytotoxic effect. No differentiation could be obtained between the smallest three oligomers tested as none of them showed a cytopathic effect at the highest concentration tested. A similar effect of the size of ethyleneimine oligomer or polymer on the cytotoxic effect was observed using MDCK cells (FIG. 4), although the effect was less gradual in this case, with a sharp decrease of cytotoxicity of oligomers below 189 Da.

Figure 5:
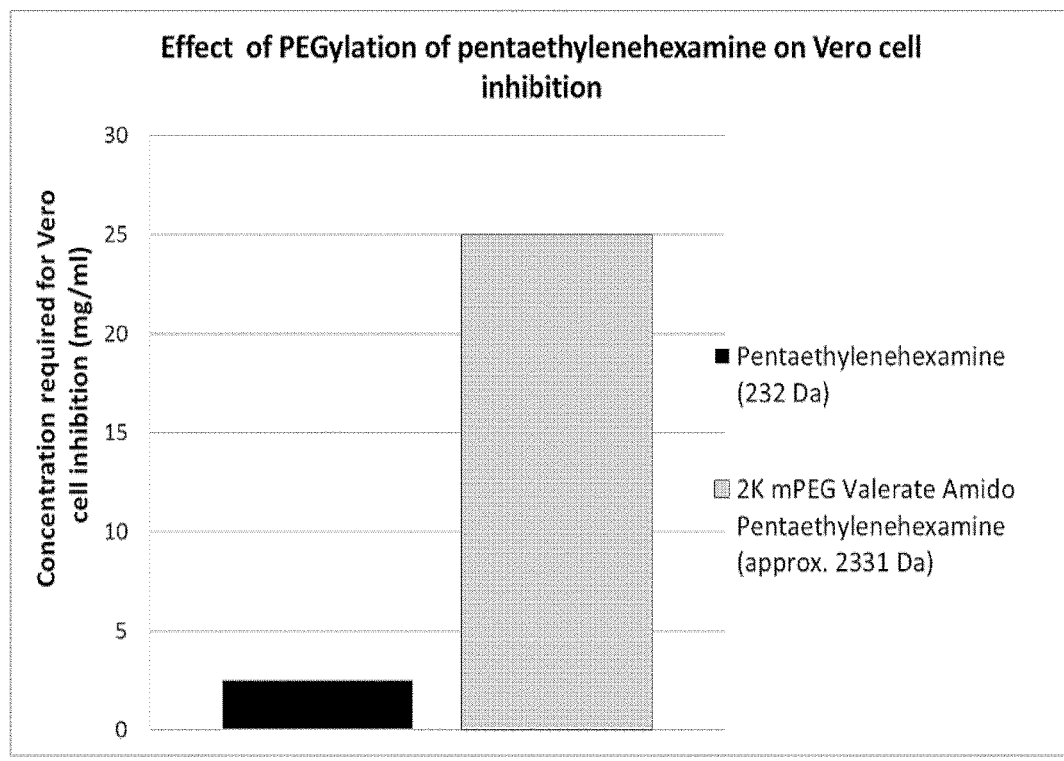
FIG. 5 shows the effect of the pentaethylenehexamine and 2K mPEG Valerate Amido Pentaethylenehexamine (Compound (1)) on Vero cell inhibition.

Example 9: Effect of PEGylation of Pentaethylenehexamine on Cytotoxic Effect Using Vero Cells Vero cells were obtained and cultured as in Example 7. The cells were incubated for 24 hours at 37° C. to become confluent. After 24 hours pentaethylenehexamine (232 Da) was prepared to a stock concentration of 5 mg/mL and was pH adjusted to 7. The stock was then diluted in DMEM+2% FBS+4 mM L-Glutamine to the following concentrations: 2.5 mg/mL, 1.25 mg/mL, 600 µg/mL, 300 µg/mL, 150 µg/mL, 75 µg/mL, 25 µg/mL, 10 µg/mL and 5 µg/mL. 2K mPEG Valerate Amido Pentaethylenehexamine (Compound (1)) was prepared from stock at 100 mg/ml using the same buffer conditions and pH to the following concentrations: 50 mg/ml, 25 mg/ml, 12.5 mg/ml, 6 mg/ml, 3 mg/ml, 1.5 mg/ml, 750 µg/ml, 250 µg/ml, 125 µg/ml and 60 µg/ml. Following the dilution step 100 µL of all of the concentrations, including the stock concentration, were added to 8 wells/plate, giving 8 replicates/concentration. The plates were incubated at 37° C. for 72 hours before being screened for Vero cell inhibition. The cytotoxic effect of pentaethylenehexamine (232 Da) was compared with that of 2K mPEG Valerate Amido Pentaethylenehexamine (Compound (1)). The concentration of 2K mPEG Valerate Amido Pentaethylenehexamine (Compound (1)) required to cause the cytotoxic effect was shown to be approximately 10 times higher than that of non-PEGylated pentaethylenehexamine (FIG. 5). This observation could possibly be explained by the fact that the pentaethylenehexamine portion of 2K mPEG Valerate Amido Pentaethylenehexamine is approximately 10% by weight.

Throughout the specification and the claims which follow, unless the context requires otherwise, the word 'comprise', and variations such as 'comprises' and 'comprising', will be understood to imply the inclusion of a stated integer, step, group of integers or group of steps but not to the exclusion of any other integer, step, group of integers or group of steps.

While this invention has been particularly shown and described with references to preferred embodiments thereof, it will be understood by those skilled in the art that various changes in form and details may be made therein without departing from the scope of the invention encompassed by the appended claims. It should also be understood that the embodiments described herein are not mutually exclusive and that features from the various embodiments may be combined in whole or in part in accordance with the invention.

Where aspects or embodiments of the invention are described in terms of a Markush group or other grouping of alternatives, the present invention encompasses not only the entire group listed as a whole, but also each member of the group individually and all possible subgroups of the main group, and also the main group absent one or more of the group members. The present invention also envisages the explicit exclusion of one or more of any of the group members in the claimed invention.

The term "and/or" as used in a phrase such as "A and/or B" herein is intended to include both A and B; A or B; A (alone); and B (alone). Likewise, the term "and/or" as used in a phrase such as "A, B, and/or C" is intended to encompass each of the following embodiments: A, B, and C; A, B, or C; A or C; A or B; B or C; A and C; A and B; B and C; A (alone); B (alone); and C (alone).

The disclosure of U.S. Appl. No. 61/592,323 is herein incorporated by reference in its entirety. Moreover, all publications, patents, patent applications, internet sites, and accession numbers/database sequences (including both polynucleotide and polypeptide sequences) cited are herein incorporated by reference in their entirety for all purposes to the same extent as if each individual publication, patent, patent application, internet site, or accession number/database sequence were specifically and individually indicated to be so incorporated by reference.

The invention claimed is:

1. An aqueous solution comprising an antibody protein at a concentration of at least about 10 mg/mL and an oligomer of ethyleneimine, wherein
   (a) the aqueous solution is substantially free of a buffer with a pKa within 1 unit of the pH of the solution,
   (b) the antibody is
      (i) trastuzumab,
      (ii) rituximab,
      (iii) infliximab,
      (iv) a fusion protein comprising an active protein domain fused to one or more immunoglobulin Fc fragments, or
      (v) certolizumab pegol; and
   (c) the number of repeating units of ethyleneimine (n) in the oligomer is in the range consisting of 2 to 12.

2. The aqueous solution of claim 1, wherein the number of repeating units of ethyleneimine (n) is 3.

3. The aqueous solution of claim 1, wherein the number of repeating units of ethyleneimine (n) in the oligomer is in the range consisting of n=3 to 5.

4. The aqueous solution of claim 1, wherein the oligomer of ethyleneimine is derivatised with one or more PEG or mPEG groups.

5. The aqueous solution of claim 4, wherein the oligomer of ethyleneimine is derivatised via an optional bridging group, wherein said bridging group is selected from the group consisting of carbonyl, amide, carbamate, urea and alkylene.

6. The aqueous solution of claim 1, wherein the oligomer of ethyleneimine is selected from the group consisting of diethylenetriamine, triethylenetetramine, tetraethylenepentamine and pentaethylenehexamine.

7. The aqueous solution of claim 1, wherein 80 to 100% of the basic nitrogen centres of the oligomer of ethyleneimine are protonated.

8. The aqueous solution or method of claim 1, wherein the oligomer of ethyleneimine is present at a concentration of about 0.01 mg/mL to about 10 mg/mL.

9. The aqueous solution of claim 1, wherein the antibody protein is a therapeutic agent.

10. The aqueous solution of claim 1, wherein the antibody protein is trastuzumab, rituximab or infliximab.

11. The aqueous solution of claim 1, wherein the antibody protein is a fusion protein comprising an active protein domain fused to one or more immunoglobulin Fc fragments.

12. The aqueous solution of claim 11, wherein the antibody protein is etanercept, abatacept or belatacept.

13. The aqueous solution of claim 1, wherein the antibody protein is certolizumab pegol.

14. The aqueous solution of claim 1, wherein the antibody protein concentration is between about 25 mg/mL and about 300 mg/mL.

15. The aqueous solution of claim 1, wherein the antibody protein concentration is greater than 50 mg/mL.

16. The aqueous solution or method of claim 1, wherein the weight ratio (wt/wt) of antibody protein to the oligomer of ethyleneimine is at least 10.

17. The aqueous solution of claim 1, wherein the pI of the antibody protein is at least 7.

18. The aqueous solution of claim 17, wherein the pI of the antibody protein is in the range of 7 to 10.

19. A packaged pharmaceutical composition suitable for administration to a subject in need thereof, comprising the aqueous solution of claim 1.

20. The aqueous solution of claim 1, wherein the oligomer of ethyleneimine is triethylenetetramine.

21. The aqueous solution of claim 1, wherein the pH of the solution is in the range 5 to 7.5.

22. The aqueous solution of claim 10, wherein the pI of the antibody protein is in the range of 7 to 10.

23. The aqueous solution of claim 11, wherein the pI of the antibody protein is in the range of 7 to 10.

24. The aqueous solution of claim 1, wherein the number of repeating units of ethyleneimine (n) in the oligomer is in the range consisting of 6 to 12.

25. The aqueous solution of claim 1, wherein the number of repeating units of ethyleneimine (n) is 4.

26. The aqueous solution of claim 1, wherein the number of repeating units of ethyleneimine (n) is 5.

* * * * *